US012723583B1

(12) United States Patent

Sharkey et al.

(10) Patent No.: US 12,723,583 B1

(45) Date of Patent: Sep. 1, 2026

(54) PERISTALTIC PUMP HEAD WITH HYBRID ROLLERS AND TUBING MANIFOLD

(71) Applicants: Ryan Sharkey, Charlotte, NC (US); Joar Stenqvist, Råå (SE)

(72) Inventors: Ryan Sharkey, Charlotte, NC (US); Joar Stenqvist, Råå (SE)

( * ) Notice: Subject to any disclaimer, the term of this patent is extended or adjusted under 35 U.S.C. 154(b) by 0 days.

(21) Appl. No.: 19/281,843

(22) Filed: Jul. 28, 2025

(51) Int. Cl.

| | |
|---|---|
| ***F04B 43/12*** | (2006.01) |
| ***A61M 5/142*** | (2006.01) |
| ***A61M 60/279*** | (2021.01) |
| ***F04B 43/00*** | (2006.01) |
| ***F04B 43/08*** | (2006.01) |

(52) U.S. Cl.

CPC ..... *F04B 43/1253* (2013.01); *A61M 5/14232* (2013.01); *A61M 60/279* (2021.01); *F04B 43/0072* (2013.01); *F04B 43/08* (2013.01); *F04B 43/12* (2013.01); *F04B 43/1261* (2013.01); *F04B 43/1276* (2013.01)

(58) Field of Classification Search

CPC ............. F04B 43/1253; F04B 43/1261; F04B 43/0072; F04B 43/1276; F04B 43/08; F04B 43/12; A61M 5/14232; A61M 60/279

See application file for complete search history.

(56) References Cited

U.S. PATENT DOCUMENTS

| | | | | |
|---|---|---|---|---|
| 4,599,055 A * | 7/1986 | Dykstra | .............. | F04B 43/1284 417/477.2 |
| 7,918,657 B2 * | 4/2011 | Bobo | .................. | F04B 43/1253 417/477.3 |

* cited by examiner

*Primary Examiner* — Peter J Bertheaud

(74) *Attorney, Agent, or Firm* — Jeffrey C. Watson, Esq.; Grell & Watson Patent Attorneys LLC

(57) ABSTRACT

A peristaltic pump head with hybrid rollers and a tubing manifold includes a housing with a curved wall and adapted to secure a flexible tube within the housing. A roller assembly rotatable within the housing includes compression rollers and hybrid rollers. Each of the hybrid rollers comes into contact with the flexible tube during rotation of the roller assembly with the hybrid rollers being operative to partially decompress the flexible tube. Fluid is moved through the flexible tube by rotation of the roller assembly. A tubing manifold is included with the housing and configured for allowing a fixed length of the flexible tube in the housing by providing a fixed connection point for a first end of the flexible tube about an entrance of the housing and a fixed connection point for a second end of the flexible tube about an exit of the housing.

17 Claims, 15 Drawing Sheets

74

18,62
76
74

50
52
38
48
54
48
12
52
50
58

18,62
46
36
40
42
38
12

26

18,62
26

10
16
108,138
104,134
18
14,94,124
102,132
106,136
118,148
117,147
120,150
110,140
100,130
98,128
96,126
114,144

10
16
14,94,124
102,132
116,146
106,136
110,140
122,152
117,147
98,128
96,126
112,142
108,138

PERISTALTIC PUMP HEAD WITH HYBRID ROLLERS AND TUBING MANIFOLD

FIELD OF THE DISCLOSURE

The present disclosure relates to a head for a peristaltic pump, or the like. More specifically, the present disclosure relates to a peristaltic pump head with hybrid rollers and a tubing manifold.

BACKGROUND

Generally speaking, a peristaltic pump is a type of positive displacement pump used for pumping a variety of fluids. The fluid is contained within a flexible tube fitted inside a head with a circular casing. A rotor within the head, with at least two rollers attached to the external circumference of the rotor, compresses the flexible tube against the circular casing. As the rotor turns, the part of tube under compression closes, forcing the fluid to move through the tube. As the tube opens to its natural state after the passing of the roller, restitution fluid flow is induced to the pump.

In a peristaltic pump, the only part of the pump in contact with the fluid being pumped is the interior of the tube. This eliminates the possibility for contamination getting into the fluid and makes it easy to clean the inside surfaces of the pump. Furthermore, since there are no moving parts in contact with the fluid, peristaltic pumps are inexpensive to manufacture. Their lack of valves, seals and glands makes them comparatively inexpensive to maintain, and the use of a hose or tube makes for a relatively low-cost maintenance item compared to other pump types.

Peristaltic pumps are mainly used to pump clean or sterile fluids because the pump cannot contaminate the fluid. Peristaltic pumps can also be used to pump aggressive fluids because the fluid cannot contaminate the pump. Therefore, peristaltic pumps should be used where isolation of the fluid from the pump and the environment, and/or isolation of the pump from the fluid, is critical.

Peristaltic pumps are an excellent choice for handling a wide range of fluids, especially those with varying viscosities and those requiring specific head pressures. Their gentle, low-shear pumping action is ideal for delicate fluids like viscous solutions and suspensions that are sensitive to agitation. What's more, these pumps excel at maintaining consistent flow rates even when faced with fluctuating pressures, and their design inherently minimizes cross-contamination.

In the flexographic industry, these characteristics translate into significant advantages. Peristaltic pumps contribute to lower maintenance costs, improved productivity due to consistent performance, less ink waste, and reduced ink contamination. Furthermore, their design simplifies the process, leading to improved cleanup times.

Some prior art patents that show a peristaltic pump head used in the Flexography printing industry include: U.S. Pat. No. 6,041,709, issued to Wells on Mar. 28, 2000, Inc.; U.S. Pat. No. 5,630,711 issued to Luedtke on May 20, 1997; U.S. Pat. No. 4,552,516 issued to Stanley on Nov. 12, 1985; and U.S. Pat. No. 7,918,657 issued to Bobo, et. al. on Apr. 5, 2011.

There are many problems with the current peristaltic pump head when used in moving a fluid or delivering ink to a flexographic printing press. The peristaltic pump heads consist of plastics and other materials, which cause constant material failures when used in moving fluids in the flexographic printing environment or any environment. These failures of materials are a very expensive cost because they require maintenance and slow down production with more pump downtime. This type of pump operation is very costly to the Flexography industry where cleaning and down time is a major part of the Flexography industry cost. The current designs are very expensive when designed as heavy industry systems to overcome these failures. These systems take up a great deal of space, require periodic maintenance and are not operator friendly.

Current peristaltic pump heads may include adjustment fixtures, occlusion knobs, bladders, and other things which are attempts to prolong tube life. These things are inadequate and do not solve many problems encountered with the tube, including: the cumbersome loading and adjusting of the tube (requiring the use of tools to adjust and load the tube), tube fatigue (from the tube being compressed repeatedly) which wears down the tube and lowers the expected tube life, tube creep (the tube becomes off centered with the rollers due to hydraulic forces caused by peristalsis) which causes additional wearing down of the tube, and tube bunching or gathering at the exit of the pump head (caused from the tube being stretched towards the exit from the rollers) which causes additional wearing down of the tube and can lead to tube rupture when used for several hours of operation. These problems lead to constant tube failures and require frequent replacement of the tube. The replacement of peristaltic pump tubes in existing pumps is a difficult and time consuming procedure which forces excess down time in the Flexography printing industry.

Another issue with current peristaltic pump heads is the flow rates between the pump head used to return from the system and the pump head used to feed the system. Ideally, a volumetric flow rate difference between the two pump heads between feeding the system and returning from the system would be accomplished at any given speed or revolutions per minute (i.e. rpm). However, with current systems, this requires multiple or separate motors and controllers for each pump head, which adds to the costs and complexity of the system. Accordingly, there is clearly a need to provide a system that provides a volumetric flow rate between the two pump heads (feeding and returning) at any given speed that only requires a single motor and controller to provide such volumetric flow rates.

The instant disclosure may be designed to address at least certain aspects of the problems or needs discussed above by providing a peristaltic pump head with hybrid rollers and a tubing manifold.

SUMMARY

The present disclosure may solve the aforementioned limitations of the currently available peristaltic pump heads, or the like, by providing a peristaltic pump head with hybrid rollers and/or a tubing manifold. In select embodiments, the disclosed peristaltic pump head with hybrid rollers and/or a tubing manifold may generally include a peristaltic pump head with a first housing that may be adapted to receive a first flexible tube having a first curved wall. The first housing may be adapted to secure said first flexible tube within said first housing. A first roller assembly may be rotatable within said first housing about a first axis through said first housing. The first axis may be coaxial to the first curved wall. The first roller assembly may include at least two compression rollers and at least one hybrid roller. The at least two compression rollers may be peripherally spaced where each of the compression rollers may come successively into contact with the first flexible tube during rotation of the first roller assembly with successive compression rollers being operative to compress two portions of said first flexible tube against the first curved wall to confine a first finite volume of fluid in said first flexible tube. The at least one hybrid roller may be peripherally spaced between the compression rollers where each of the hybrid rollers may come into contact with the first flexible tube during rotation of the first roller assembly with the hybrid rollers being operative to partially decompress said first flexible tube and guide the first flexible tube to stay centered with the compression rollers. The hybrid rollers may be operative to initiate decompression of the first flexible tube to return to a partial compression dimension. Whereby the fluid in the first flexible tube may be moved through the first flexible tube by rotation of the first roller assembly.

One feature of the disclosed peristaltic pump head may be that the hybrid rollers may have a channel with a width and a depth. The width may be centered on the hybrid rollers for guiding the first flexible tube to stay centered with the compression rollers on a first horizontal plane. The depth may be configured for allowing partial decompression of the first flexible tube to the partial compression dimension. The width may be at least the width of the first flexible tube at the partial compression dimension for allowing decompression of the first flexible tube to return to the partial compression dimension. In select embodiments, the partial compression dimension allowed by the hybrid rollers may be when the first flexible tube is compressed approximately fifty percent (50%). In other select embodiments, the hybrid rollers may include a rounded transition on both sides of the channel between walls of the channel and a bottom of the channel. The rounded transition on both sides of the channel may be sized and configured for the shape of the first flexible tube at the partial compression dimension. In select embodiments of the hybrid rollers, the walls of said channel, the rounded transition of the channel, the bottom of the channel, or a combination thereof, may include an anti-friction surface. The anti-friction surface on the interior of the channel of the hybrid rollers, like on the walls of the channel, the rounded transition of the channel, and/or the bottom of the channel, may be configured for aiding the hybrid rollers to move along the first flexible tube.

In select embodiments of the disclosed peristaltic pump head, the number of the hybrid rollers in the first roller assembly may be equal to the number of the compression rollers in the first roller assembly. Wherein, one hybrid roller may be peripherally spaced between every compression roller in the first roller assembly.

In select embodiments, the disclosed peristaltic pump head may further include a second housing. The second housing may be adapted to receive a second flexible tube having a second curved wall. The second housing may be adapted to secure the second flexible tube within the second housing. In these embodiments with the second housing, a second roller assembly may be rotatable within the second housing about a second axis through the second housing. The second axis may be coaxial to the second curved wall. The second roller assembly may include at least two of the compression rollers and at least one guide roller. The at least two of the compression rollers may be peripherally spaced where each of the compression rollers coming successively into contact with the second flexible tube during rotation of the second roller assembly with successive compression rollers being operative to compress two portions of the second flexible tube against said second curved wall to confine a second finite volume of fluid in the second flexible tube. The at least one guide roller may be peripherally spaced between the compression rollers. Each of the guide rollers may come into contact with the second flexible tube during rotation of the second roller assembly with the guide rollers being operative to fully decompress the second flexible tube and guide the second flexible tube to stay centered with the compression rollers. The guide rollers may be operative to initiate decompression of the second flexible tube to return to a fully uncompressed dimension. Whereby fluid may be moved through the second flexible tube by rotation of the second roller assembly in the second housing.

In select embodiments of the disclosed peristaltic pump head, the number of the guide rollers in the second roller assembly may be equal to the number of the compression rollers in the second roller assembly. Whereby, one guide roller may be peripherally spaced between every compression roller in the second roller assembly.

One feature of the disclosed peristaltic pump head may be that the first roller assembly and the second roller assembly can be controlled by a single motor with a single controller. Whereby, the speed of rotation of the first roller assembly and the second roller assembly may be the same. In select embodiments of the disclosed peristaltic pump head, the first housing with the first roller assembly of compression rollers and hybrid rollers may be configured for feeding the fluid to a system via the first flexible tube. On the other hand, the second housing with the second roller assembly of compression rollers and guide rollers may be configured for returning the fluid from the system via the second flexible tube. Wherein a volumetric fluid flow rate may be created between the fluid moving in the first flexible tube (feeding the system) via the first roller assembly and the fluid moving in the second flexible tube (returning from the system) via the second roller assembly. The volumetric fluid flow rate created between the fluid moving in the first flexible tube via the first roller assembly and the fluid moving in the second flexible tube via the second roller assembly may be provided at any given speed of the motor. In select embodiments, the volumetric fluid flow rate created between the fluid moving in the first flexible tube (feeding the system) via the first roller assembly and the fluid moving in the second flexible tube (returning from the system) via the second roller assembly may be ten percent (10%) to fifteen percent (15%) greater in the fluid moving in the second flexible tube (returning) than the fluid moving in the first flexible tube (feeding).

Another feature of the disclosed peristaltic pump head may be that the first housing may be adapted to load the first flexible tube. Whereby, when said first flexible tube is inserted into a first entrance and said first roller assembly is rotated, the hybrid rollers and the compression rollers guiding the first flexible tube around the first roller assembly and out of a first exit. Likewise, the second housing may be adapted to load the second flexible tube. Whereby, when the second flexible tube is inserted into a second entrance and the second roller assembly is rotated, the guide rollers and the compression rollers guiding the second flexible tube around the second roller assembly and out of a second exit.

Another feature of the disclosed peristaltic pump head may be the inclusion of a first tubing manifold with the first housing. The first tubing manifold may be configured for allowing a fixed length of the first flexible tube in the first housing by providing a fixed connection point for a first end of the first flexible tube about a first entrance of the first housing and a fixed connection point for a second end of the first flexible tube about a first exit of the first housing. In select embodiments, the first tubing manifold may include a first bracket attached to a first side of the first housing. The first bracket may extend from the first side of the first housing away from the first entrance and the first exit. A first mounting flange may extend perpendicular to the first bracket in front of the first entrance and the first exit. The fixed connection point for the first end of the first flexible tube and the fixed connection point for the second end of the first flexible tube may be attached or affixed on the first mounting flange. Wherein, the first mounting flange may be configured to position the fixed connection point for the first end of the first flexible tube in line with the first entrance of the first housing and the fixed connection point for the second end of the first flexible tube in line with the first exit of the first housing.

One feature of the disclosed peristaltic pump head may be that the first bracket of the first tubing manifold may include a first adjustable connection to the first side of the first housing. The first adjustable connection may be configured for allowing the first bracket to adjust the first mounting flange towards and away from the first housing. Whereby a first connection length can be adjusted between the fixed connection point for the first end of the first flexible tube and the first entrance of the first housing and the fixed connection point for the second end of the first flexible tube and the first exit of the first housing. Whereby the first bracket may be adjusted for properly tensioning the first flexible tube around the first roller assembly.

Another feature of the disclosed peristaltic pump head may be that the first adjustable connection of the first bracket to the first side of the first housing may be configured to allow the first bracket to rotate about the first side of the first housing. Wherein, the first bracket rotating up or down about the first side of the first housing may be configured to aid in allowing the changing out of the first flexible tube from the first housing.

In select embodiments of the disclosed peristaltic pump head, the first adjustable connection of the first tubing manifold to the first side of the first housing may include a first longitudinal slot, a first threaded hole and a first screw with a first knob handle. The first longitudinal slot may be in the first bracket of the first tubing manifold. A first base plate may be affixed to the first side of the first housing with a first threaded hole therein. A first screw with a first knob handle may be configured to go through the first longitudinal slot and engage the first threaded hole in the first base plate. Wherein, the first screw may be configured to be screwed into the first threaded hole via the first knob handle for securely affixing the first bracket about the first side of the first housing. In reverse, the first screw may be configured to be loosened via the first knob handle for adjusting the first mounting flange towards and away from the first housing, or for rotating the first bracket about the first side of the first housing, like for changing out of the first flexible tube from the first housing.

In select embodiments of the disclosed peristaltic pump head, the first tubing manifold may be included with the first housing and a second tubing manifold may be included with the second housing. The second tubing manifold may be configured for allowing a fixed length of said second flexible tube in the second housing by providing a fixed connection point for a first end of the second flexible tube about a second entrance of the second housing and a fixed connection point for a second end of the second flexible tube about a second exit of the second housing. In select embodiments, the second tubing manifold may include a second bracket attached to a second side of the second housing. The second bracket may extend from the second side of the second housing away from the second entrance and the second exit. A second mounting flange may extend perpendicular to the second bracket in front of the second entrance and the second exit. The fixed connection point for the first end of the second flexible tube and the fixed connection point for the second end of the second flexible tube may be attached or affixed on the second mounting flange. Wherein, the second mounting flange may be configured to position the fixed connection point for the first end of the second flexible tube in line with the second entrance of the second housing and the fixed connection point for the second end of the second flexible tube in line with the second exit of the second housing.

One feature of the disclosed peristaltic pump head may be that the second bracket of the second tubing manifold may include a second adjustable connection to the second side of the second housing. The second adjustable connection may be configured for allowing the second bracket to adjust the second mounting flange towards and away from the second housing. Whereby a second connection length can be adjusted between the fixed connection point for the first end of the second flexible tube and the second entrance of the second housing and the fixed connection point for the second end of the second flexible tube and the second exit of the second housing. Whereby the second bracket may be adjusted for properly tensioning the second flexible tube around the second roller assembly.

Another feature of the disclosed peristaltic pump head may be that the second adjustable connection of the second bracket to the second side of the second housing may be configured to allow the second bracket to rotate about the second side of the second housing. Wherein, the second bracket rotating up or down about the second side of the second housing may be configured to aid in allowing the changing out of the second flexible tube from the second housing.

In select embodiments of the disclosed peristaltic pump head, the second adjustable connection of the second tubing manifold to the second side of the second housing may include a second longitudinal slot, a second threaded hole and a second screw with a second knob handle. The second longitudinal slot may be in the second bracket of the second tubing manifold. A second base plate may be affixed to the second side of the second housing with a second threaded hole therein. A second screw with a second knob handle may be configured to go through the second longitudinal slot and engage the second threaded hole in the second base plate. Wherein, the second screw may be configured to be screwed into the second threaded hole via the second knob handle for securely affixing the second bracket about the second side of the second housing. In reverse, the second screw may be configured to be loosened via the second knob handle for adjusting the second mounting flange towards and away from the second housing, or for rotating the second bracket about the second side of the second housing, like for changing out of the second flexible tube from the second housing.

In another aspect, the instant disclosure embraces a peristaltic pump head in any of the various embodiments and/or combinations of embodiments shown and/or described herein.

In another aspect, the instant disclosure embraces a peristaltic pump in any of the various embodiments and/or combinations of embodiments shown and/or described herein.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

The present apparatuses, systems and methods will be better understood by reading the disclosure with reference to the accompanying drawings, which are not necessarily drawn to scale, and in which like reference numerals denote similar structure and refer to like elements throughout, and in which.

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

DETAILED DESCRIPTION

Referring now to FIGS. 1-23, in describing the exemplary embodiments of the present disclosure, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples and are merely examples among other possible examples.

Referring to FIGS. 1-23, the present disclosure may solve the aforementioned limitations of the currently available peristaltic pumps and peristaltic pump heads, by providing the disclosed peristaltic pump head 10. Peristaltic pump head 10 may generally include hybrid rollers 12 and/or tubing manifold 14. Hybrid rollers 12 may generally be for providing a volumetric flow rate to another pump head without hybrid rollers. Hybrid rollers 12 may be included in a single pump head configuration of a peristaltic pump, or a multiple pump head configuration of a peristaltic pump, including, but not limited to the two pump head configuration shown in FIGS. 1-3. Tubing manifold 14 may generally be for allowing a fixed length of the flexible tubing in the pump housing by providing a fixed connection point for a first end of the flexible tubing about an entrance of the first housing and a fixed connection point for a second end of the flexible tubing about an exit of the first housing. Tubing manifold 14 and/or multiple tubing manifolds 14 may be included in a single pump head configuration of a peristaltic pump, or a multiple pump head configuration of a peristaltic pump, including, but not limited to the two pump head configuration shown in FIGS. 1-3 with two tubing manifolds 14. The disclosed peristaltic pump head 10 may include various embodiments and/or combinations of embodiments of hybrid rollers 12 and/or tubing manifold 14 with various configurations of peristaltic pump head 10.

Figures 15A, 15B, 16A, 16B, 17A, 17B:
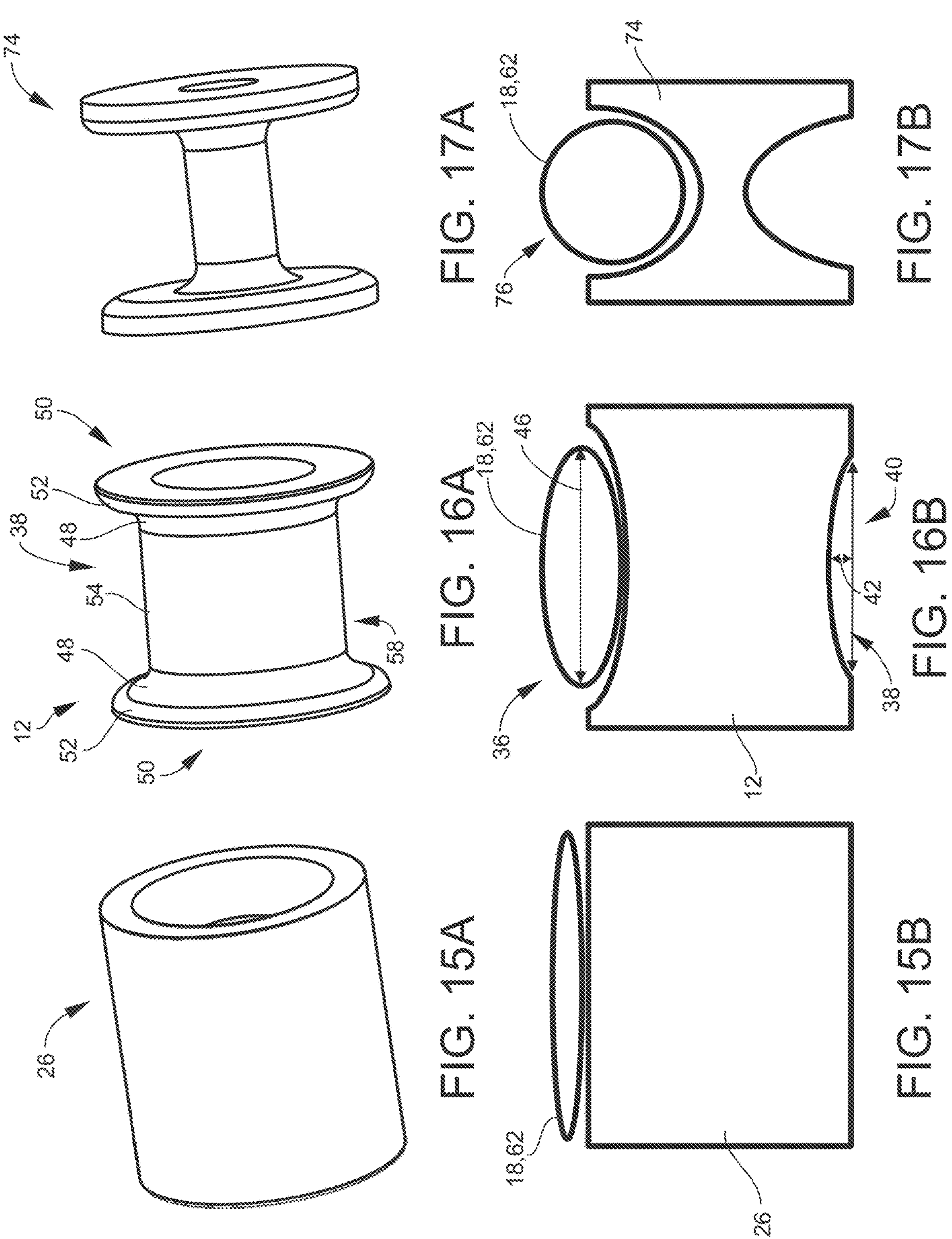
FIG. 15A is another perspective view of the compression roller from FIG. 12.
FIG. 15B is a side schematic view of the compression roller from FIG. 12 fully compressing the flexible tube of the disclosed peristaltic pump head.
FIG. 16A is another perspective view of the compression roller from FIG. 13.
FIG. 16B is a side schematic view of the hybrid roller from FIG. 13 partially compressing the flexible tube of the disclosed peristaltic pump head.
FIG. 17A is another perspective view of the compression roller from FIG. 14.
FIG. 17B is a side schematic view of the guide roller from FIG. 14 merely guiding the flexible tube of the disclosed peristaltic pump head with no compression on the flexible tube.
Figures 18, 19:
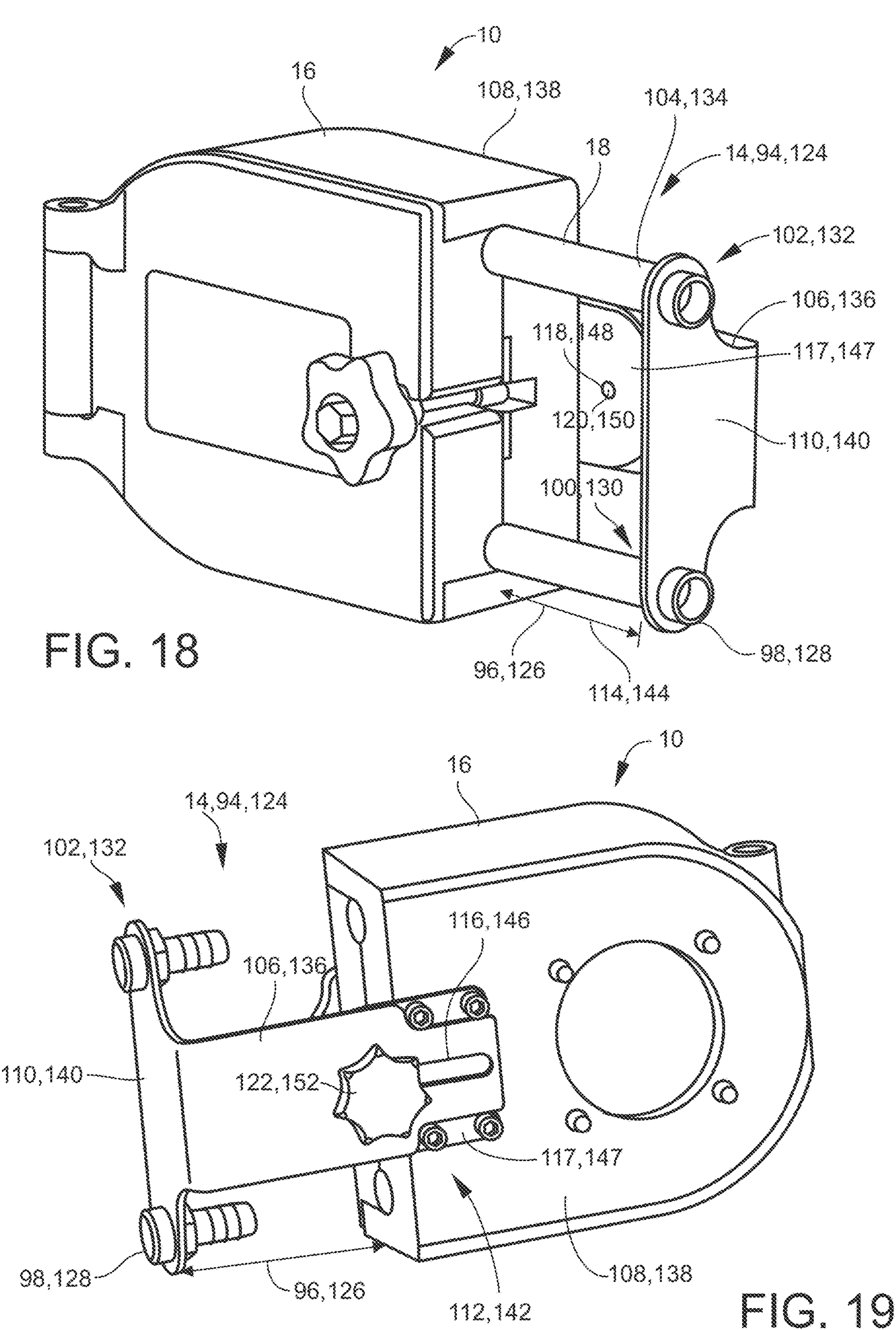
FIG. 18 is a side perspective view of the pump head with the tubing manifold attached thereto for the disclosed peristaltic pump head according to select embodiments of the instant disclosure.
FIG. 19 is an opposite side perspective view of the pump head with the tubing manifold attached thereto from FIG. 18.
Figures 20, 21:
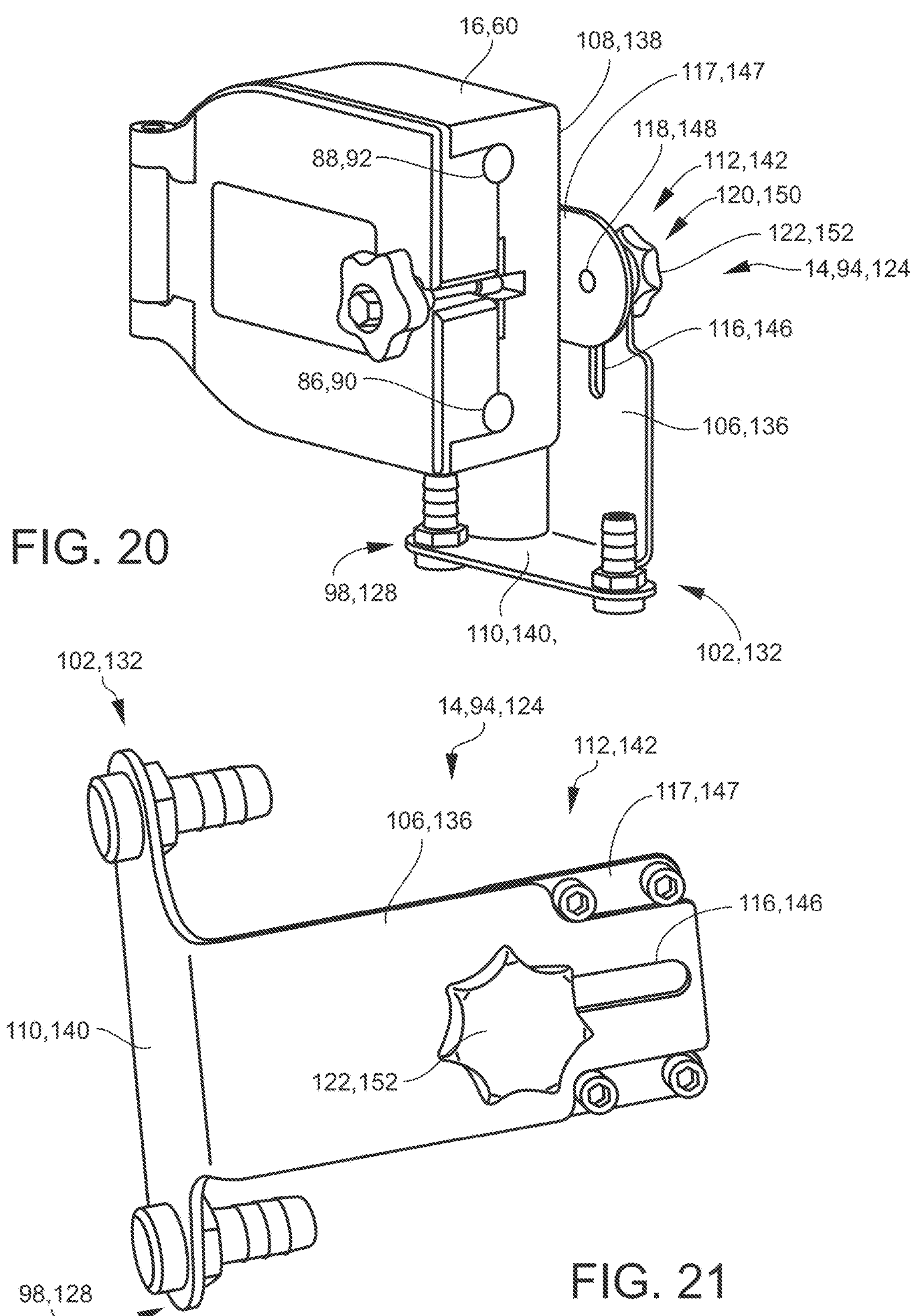
FIG. 20 another side perspective view of the pump head with the tubing manifold attached thereto from FIG. 18 with the tubing manifold rotated away from the pump head for changing the flexible tubing.
FIG. 21 is a side perspective view of the tubing manifold for the disclosed peristaltic pump head according to select embodiments of the instant disclosure.
Figure 22:
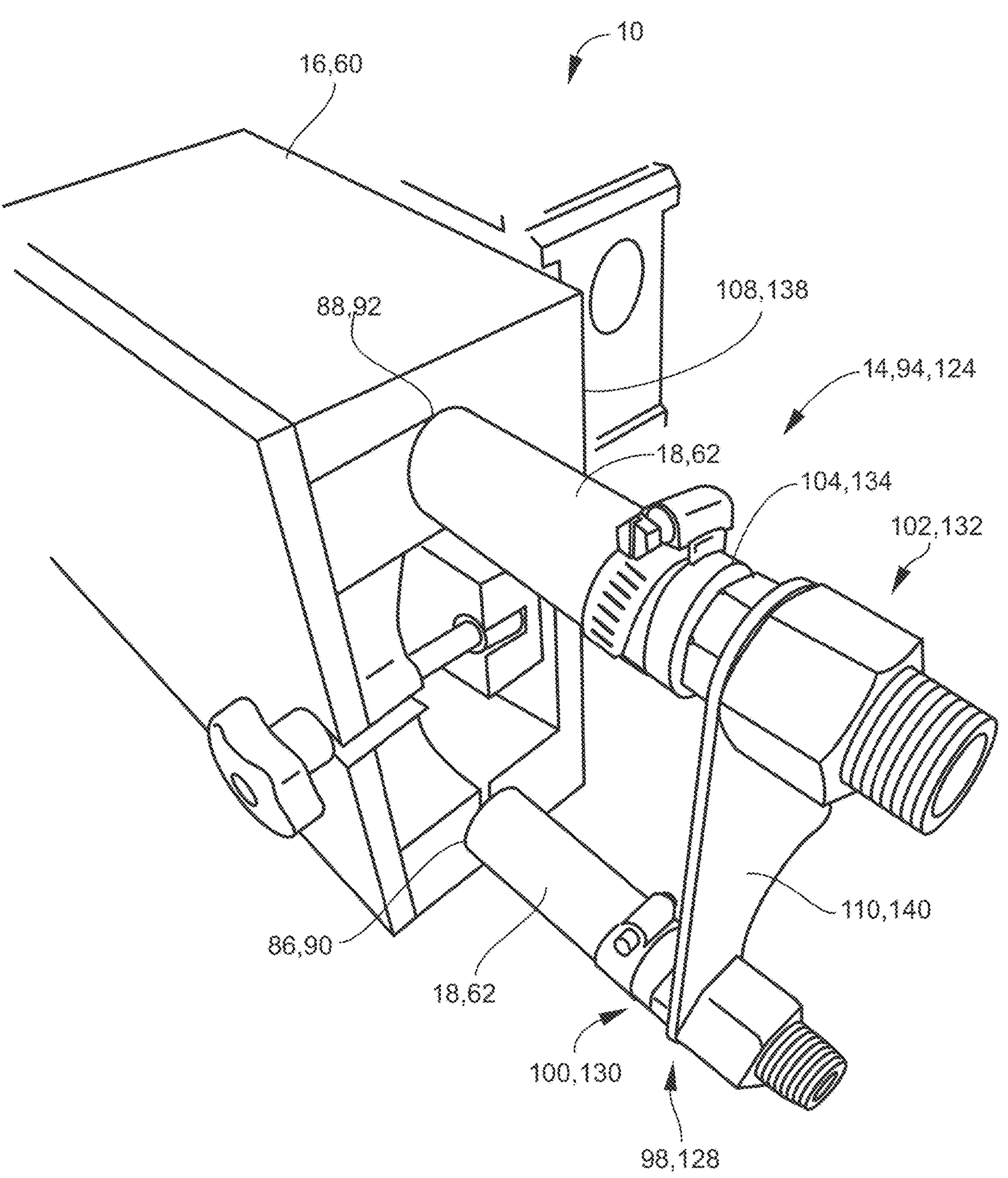
FIG. 22 is a side perspective view of the pump head with the tubing manifold attached thereto for the disclosed peristaltic pump head according to select embodiments of the instant disclosure with the flexible tubing connected thereto.

In select embodiments, peristaltic pump head 10 with hybrid rollers 12 and/or tubing manifold 14 may generally include peristaltic pump head 10 with first housing 16. As shown best in FIG. 2, housing 16 may be adapted to receive first flexible tube 18. First housing 16 may have first curved wall 20. First housing 16 may be adapted to secure first flexible tube 18 within first housing 16. First roller assembly 22 may be rotatable within first housing 16 about first axis 24 through first housing 16. First axis 24 may be coaxial to first curved wall 20 of first housing 16. First roller assembly 22 may include at least two compression rollers 26 and at least one hybrid roller 12. The compression rollers 26 may be peripherally spaced where each of the compression rollers 26 may come successively into contact with first flexible tube 18 during rotation of first roller assembly 22 with successive compression rollers 26 being operative to compress two portions 28 of said first flexible tube 18 against first curved wall 20 to confine first finite volume 30 of fluid 32 in first flexible tube 18. The at least one hybrid roller 12 of first roller assembly 22 may be peripherally spaced between compression rollers 26 where each of the hybrid rollers 12 may come into contact with first flexible tube 18 during rotation of first roller assembly 22 with hybrid rollers 12 being operative to partially decompress first flexible tube 18 and guide first flexible tube 18 to stay centered with compression rollers 26 in first housing 16. Hybrid rollers 12 may be operative to initiate decompression of first flexible tube 18 to return to partial compression dimension 36, as best shown in FIG. 16B. Whereby, fluid 32 in first flexible tube 18 may be moved through first flexible tube 18 by rotation of first roller assembly 22. As shown in the Figures, namely FIG. 2, in select embodiments first housing 16 may have a hinged door for accessing first flexible tube 18 inside of first housing 16, like for fixing and/or replacing first flexible tube 18.

Hybrid rollers 12 may be included with one or more of the roller assemblies in peristaltic pump head 10, including, but not limited to, on first roller assembly 22 in first housing 16. See FIGS. 2, 5, 8, 11, 13, 16A, and 16B. Hybrid rollers 12 may be designed and configured to change the flow rate of fluid created by peristaltic pump 10. Hybrid rollers 12 may be sized and configured to provide various amounts of change to the flow rate of fluid created by peristaltic pump 10. One feature of peristaltic pump head 10 may be that hybrid rollers 12 may have channel 38 with width 40 and depth 42. See FIGS. 5, 7, 11, 13, 16A and 16B. Width 40 may be centered on hybrid rollers 12 for guiding first flexible tube 18 to stay centered with compression rollers 26 on first horizontal plane 44. Depth 42 may be configured for allowing partial decompression of first flexible tube 18 to partial compression dimension 36. Width 40 may be at least width 46 of first flexible tube 18 at partial compression dimension 36 for allowing decompression of first flexible tube 18 to return to partial compression dimension 36. See FIG. 16B. In select possibly preferred embodiments, partial compression dimension 36 allowed by the hybrid rollers 12 may be, but is not limited to when first flexible tube 18 is compressed approximately fifty percent (50%). In other select embodiments, hybrid rollers 12 may include rounded transition 48 on both sides 50 of channel 38 between walls 52 of channel 38 and bottom 54 of channel 38. The rounded transition 48 on both sides 50 of channel 38 may be sized and configured for the shape of first flexible tube 18 at partial compression dimension 36. In select embodiments of hybrid rollers 12, walls 52 of channel 38, rounded transitions 48 of channel 38, and/or bottom 54 of channel 38, may include anti-friction surface 58. Anti-friction surface 58 on the interior of channel 38 of the hybrid rollers 12, like on walls 52 of channel 38, the rounded transitions 48 of channel 38, and/or bottom 54 of channel 38, may be configured for aiding hybrid rollers 12 to move along first flexible tube 18. Anti-friction surface 58 on the interior of channel 38 may be any anti-friction surface, like a slippery coating, material, roller bearings, or the like.

In select embodiments of peristaltic pump head 10, as shown in the Figures, the number of hybrid rollers 12 in first roller assembly 22 may be equal to the number of compression rollers 26 in first roller assembly 22. Wherein, one hybrid roller 12 may be peripherally spaced between every compression roller 26 in first roller assembly 22. As shown in the Figures, is select possibly preferred embodiments, two compression rollers 26 and two hybrid rollers 12 may be included with first roller assembly 22.

Figure 1:
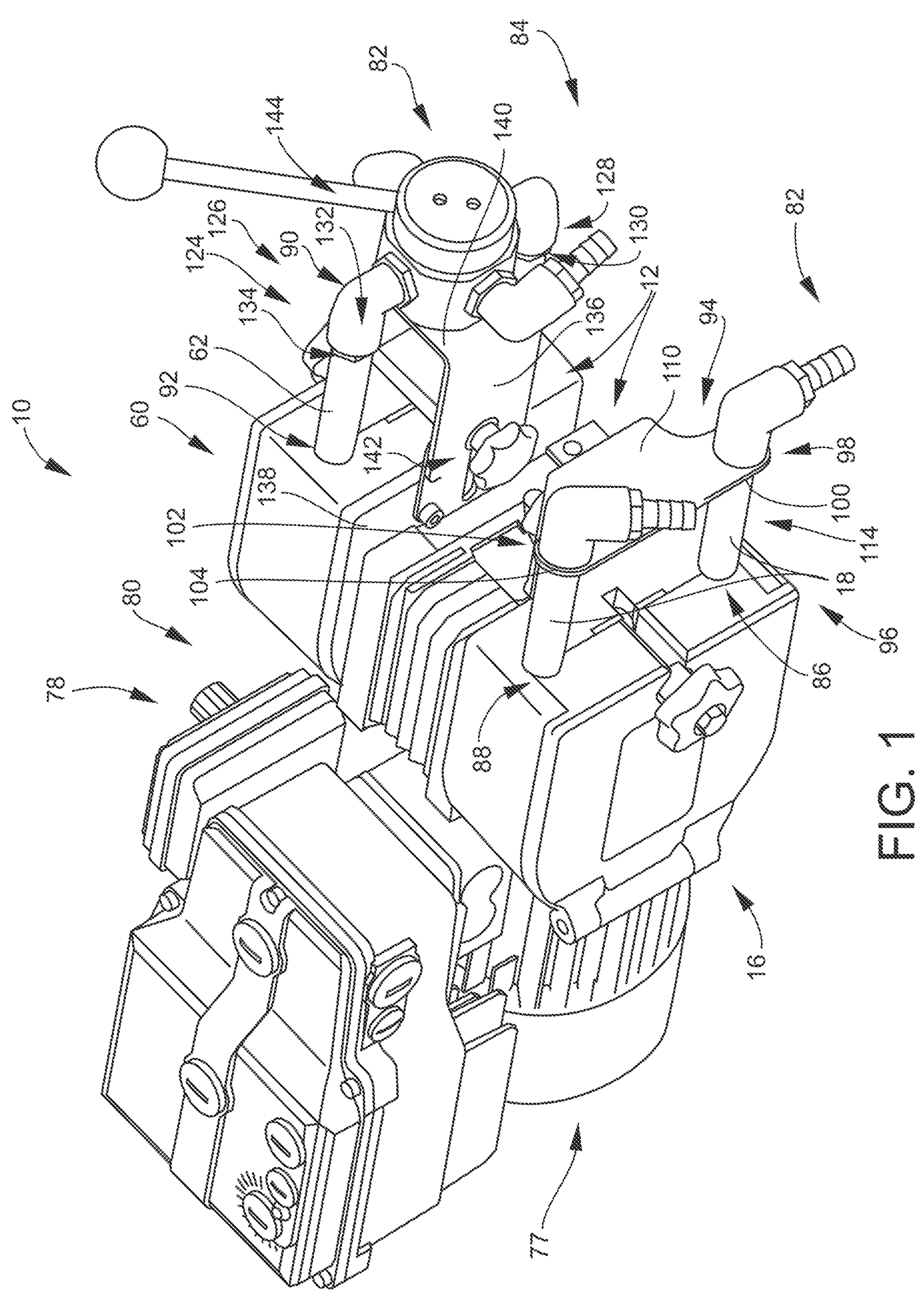
FIG. 1 is a perspective view of a peristaltic pump head with hybrid rollers and a tubing manifold according to select embodiments of the instant disclosure.
Figure 2:
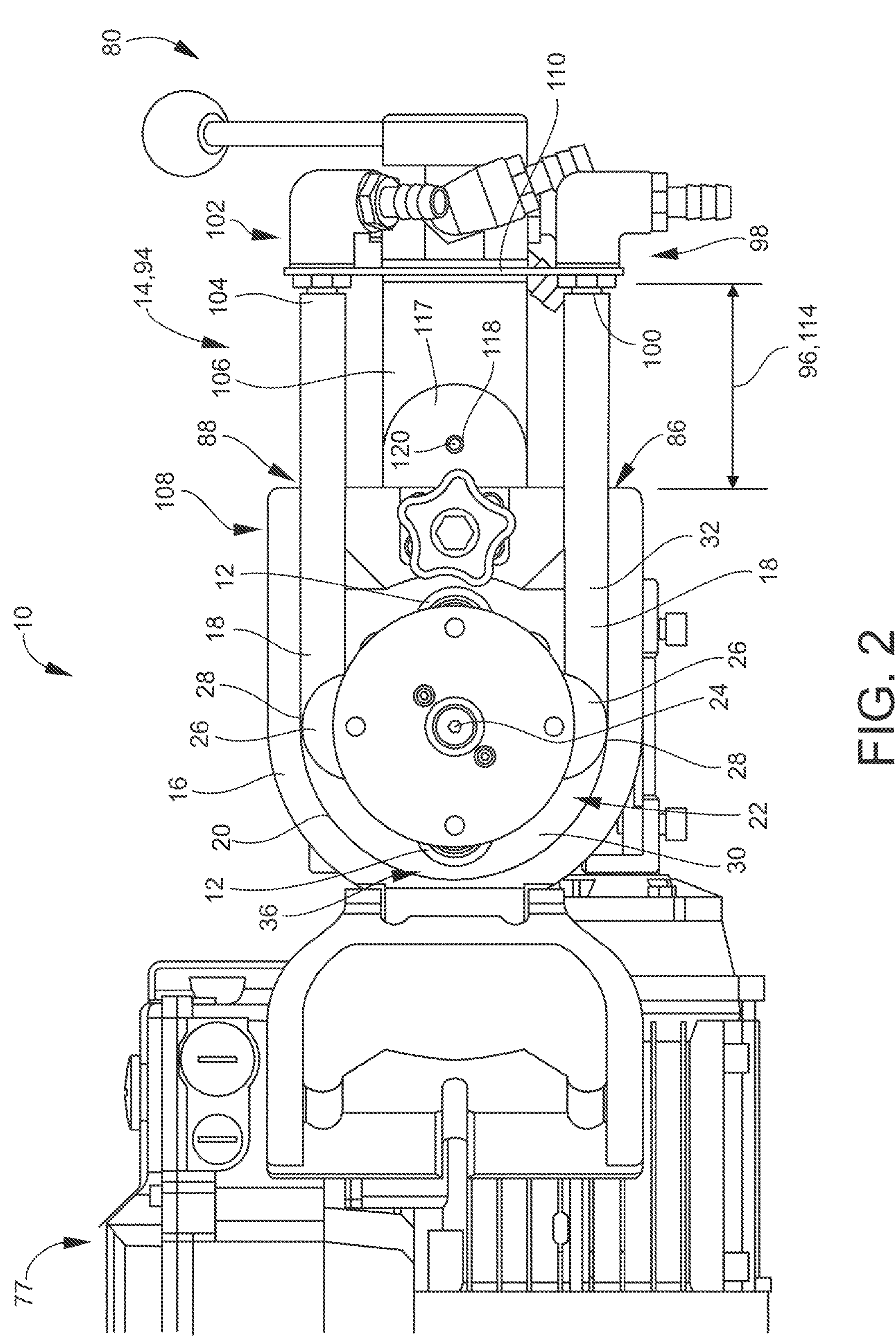
FIG. 2 is a left side view of the peristaltic pump head from FIG. 1 with the left side door open showing the left side pump roller assembly with compression rollers and guide rollers with the tubing connected to the left side tubing manifold.
Figure 3:
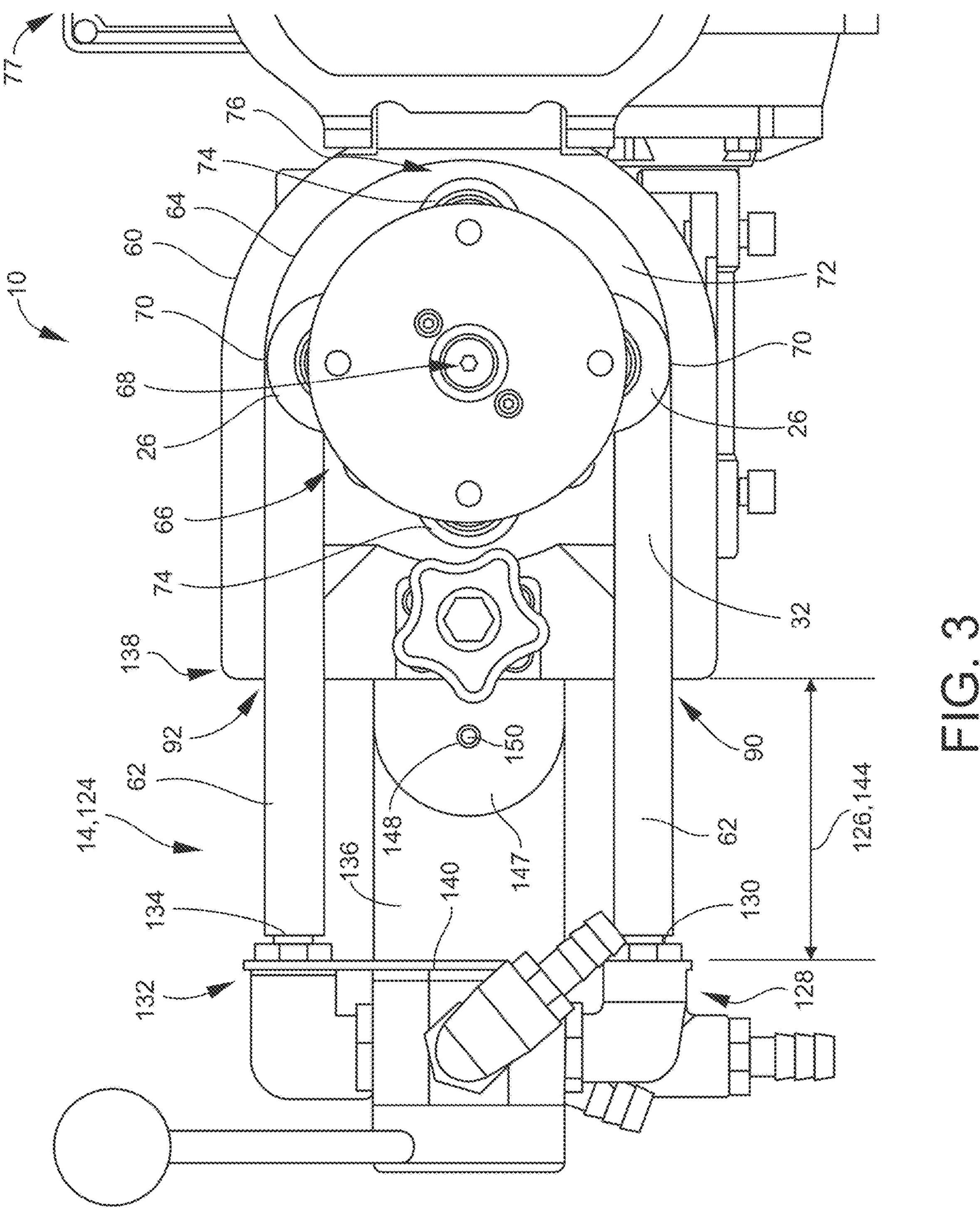
FIG. 3 is a right side view of the peristaltic pump head from FIG. 1 with the right side door open showing the right side pump roller assembly with compression rollers and hybrid rollers with the tubing connected to the right side tubing manifold.

As shown in FIGS. 1-3, in select embodiments, peristaltic pump head 10 may further include second housing 60. Peristaltic pump head 10 with first housing 16 and second housing 60 provided a two pump head configuration for peristaltic pump head 10. Second housing 60 may be adapted to receive second flexible tube 62 and may have second curved wall 64. Second housing 60 may be adapted to secure second flexible tube 62 within second housing 60. In these two pump head configuration embodiments with second housing 60, second roller assembly 66 may be rotatable within second housing 60 about second axis 68 through second housing 60. Second axis 68 may be coaxial to second curved wall 64. As best shown in FIGS. 3, 4, 6, 9, and 10, second roller assembly 66 may include at least two of the compression rollers 26 and at least one guide roller 74. The compression rollers 26 may be peripherally spaced where each of the compression rollers 26 coming successively into contact with second flexible tube 62 during rotation of second roller assembly 66 with successive compression rollers 26 being operative to compress two portions 70 of second flexible tube 62 against second curved wall 64 to confine second finite volume 72 of fluid 32 in second flexible tube 62. The at least one guide roller 74 may be peripherally spaced between the compression rollers 26. Each of the guide rollers 74 may come into contact with second flexible tube 62 during rotation of second roller assembly 66 with the guide rollers 74 being operative to fully decompress second flexible tube 62 and guide second flexible tube 62 to stay centered with compression rollers 26 around second roller assembly 66 in second housing 60. The guide rollers 74 may be operative to initiate decompression of second flexible tube 62 to return to fully uncompressed dimension 76. See FIG. 17B. Whereby, fluid 32 may be moved through second flexible tube 62 by rotation of second roller assembly 66 in second housing 60. Like first housing 16, second housing 60 may have a hinged door for accessing second flexible tube 62 inside of second housing 60, like for fixing and/or replacing second flexible tube 62.

Figure 4:
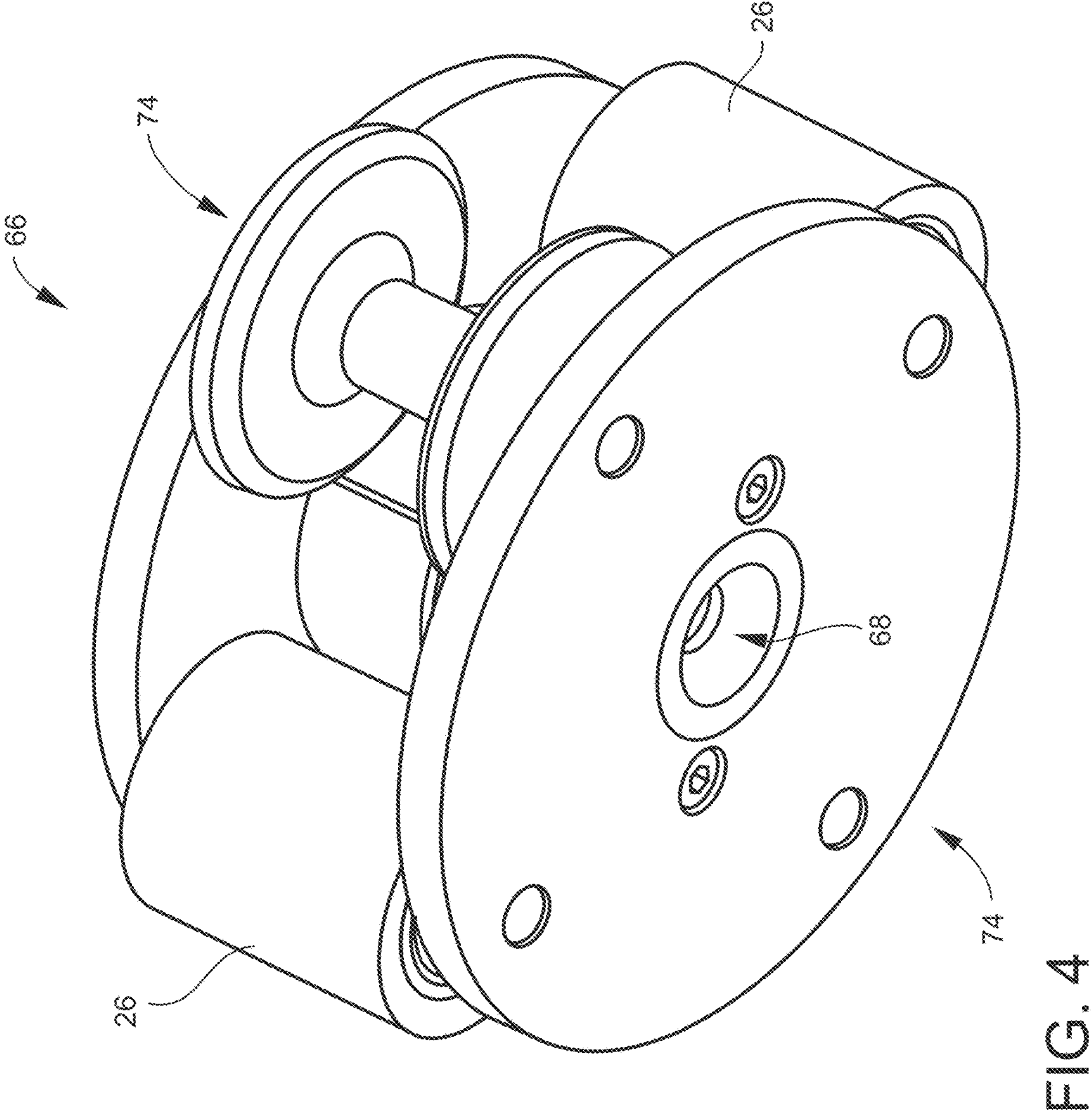
FIG. 4 is a perspective view of a roller assembly for the disclosed peristaltic pump head according to select embodiments of the instant disclosure with compression rollers and guide rollers.
Figure 5:
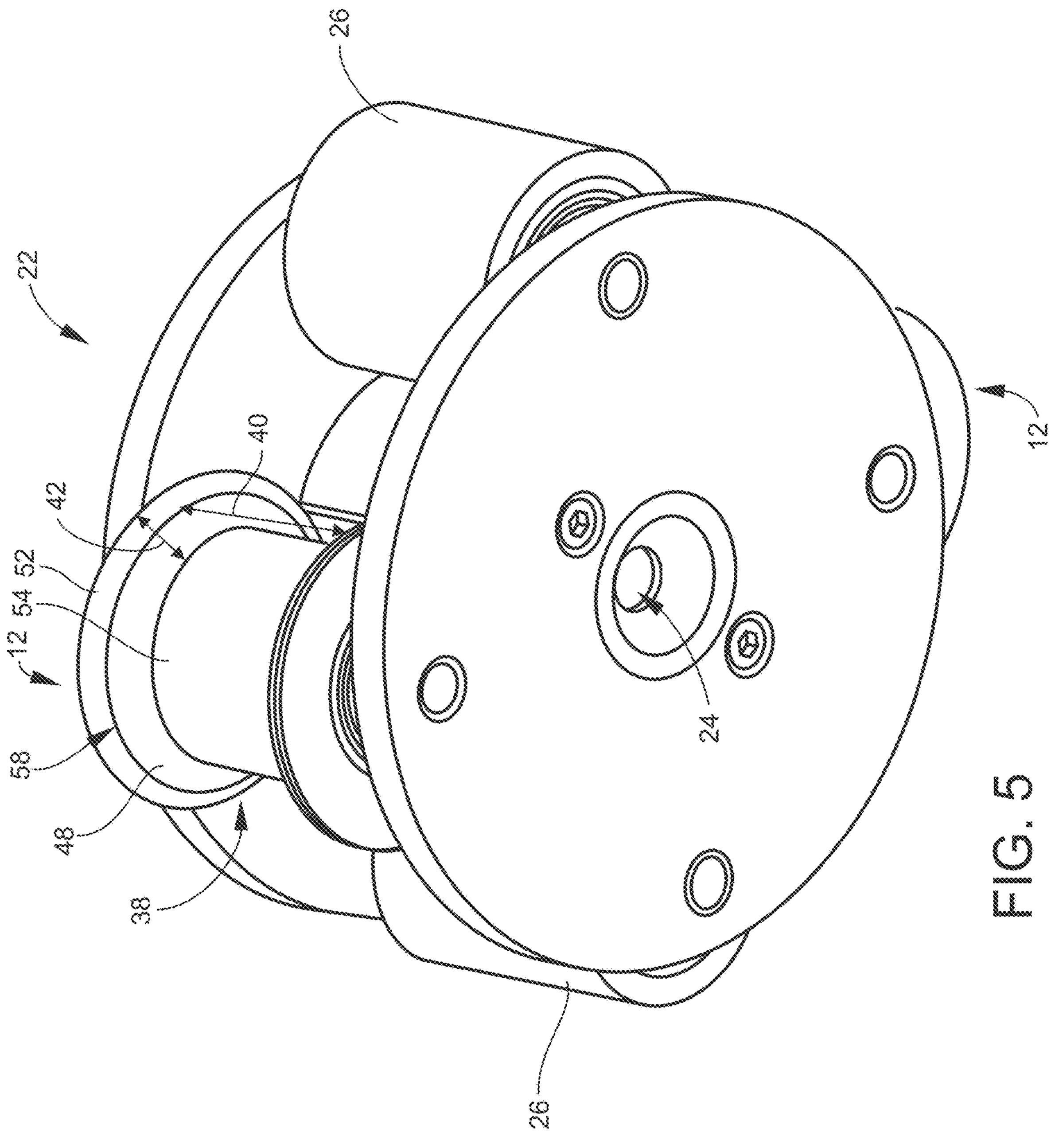
FIG. 5 is a perspective view of a roller assembly for the disclosed peristaltic pump head according to select embodiments of the instant disclosure with compression rollers and hybrid rollers.
Figures 6, 7:
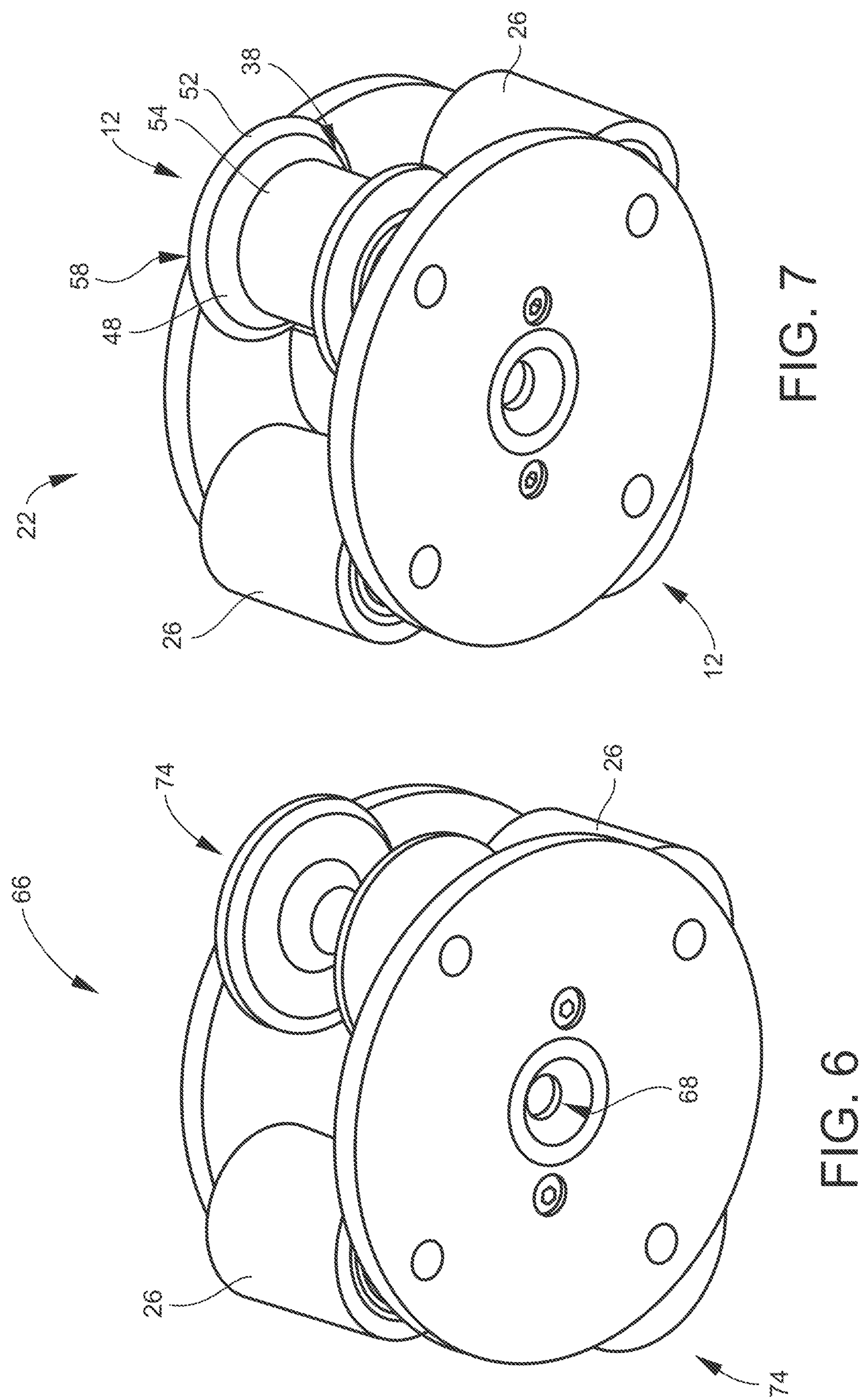
FIG. 6 is another perspective view of the roller assembly from FIG. 4 with compression rollers and guide rollers.
FIG. 7 is a perspective view of the roller assembly from FIG. 5 with compression rollers and hybrid rollers.
Figures 8, 9:
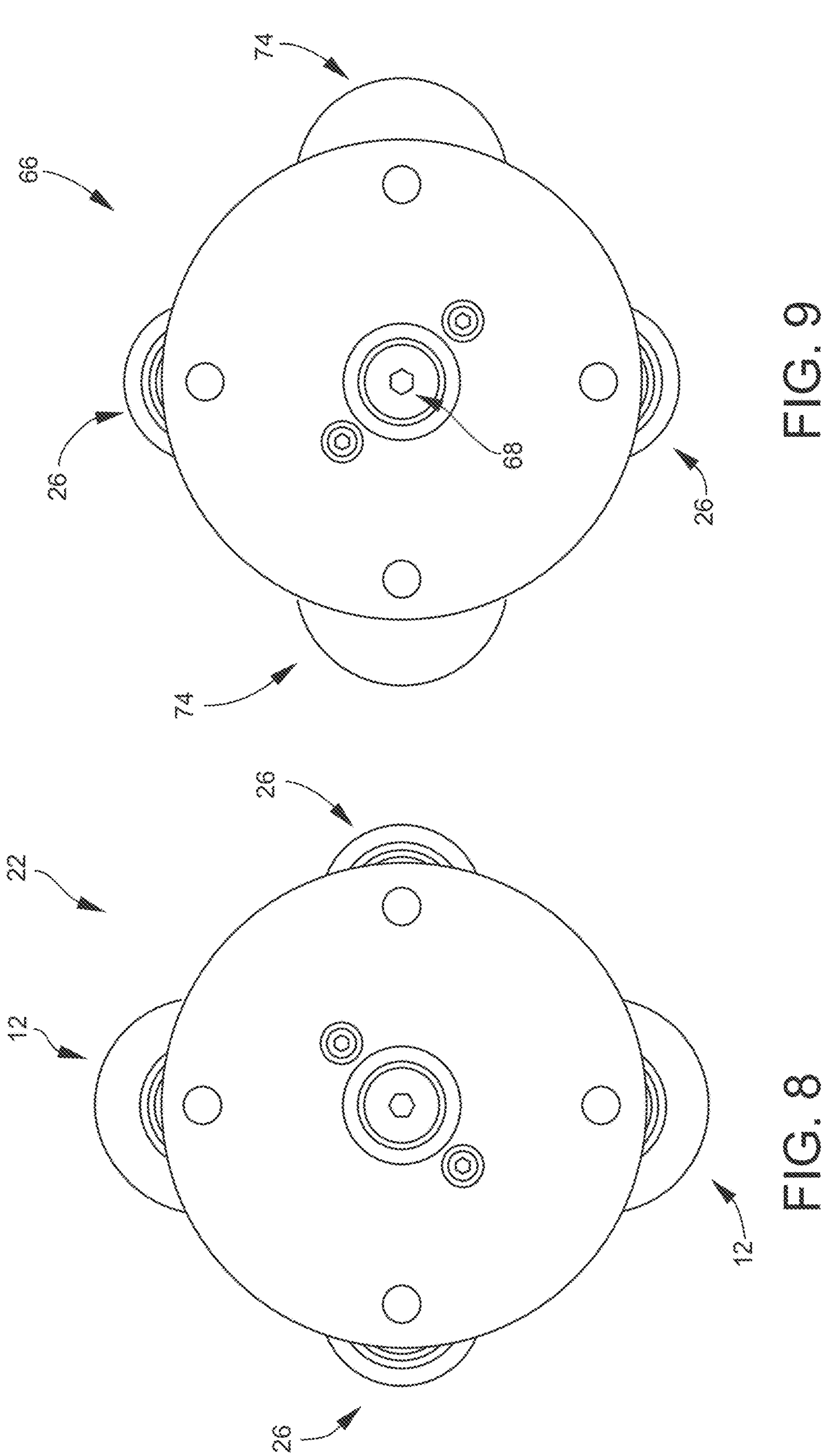
FIG. 8 is a side view of the roller assembly from FIG. 4 with compression rollers and guide rollers.
FIG. 9 is a perspective view of the roller assembly from FIG. 5 with compression rollers and hybrid rollers.
Figures 10, 11:
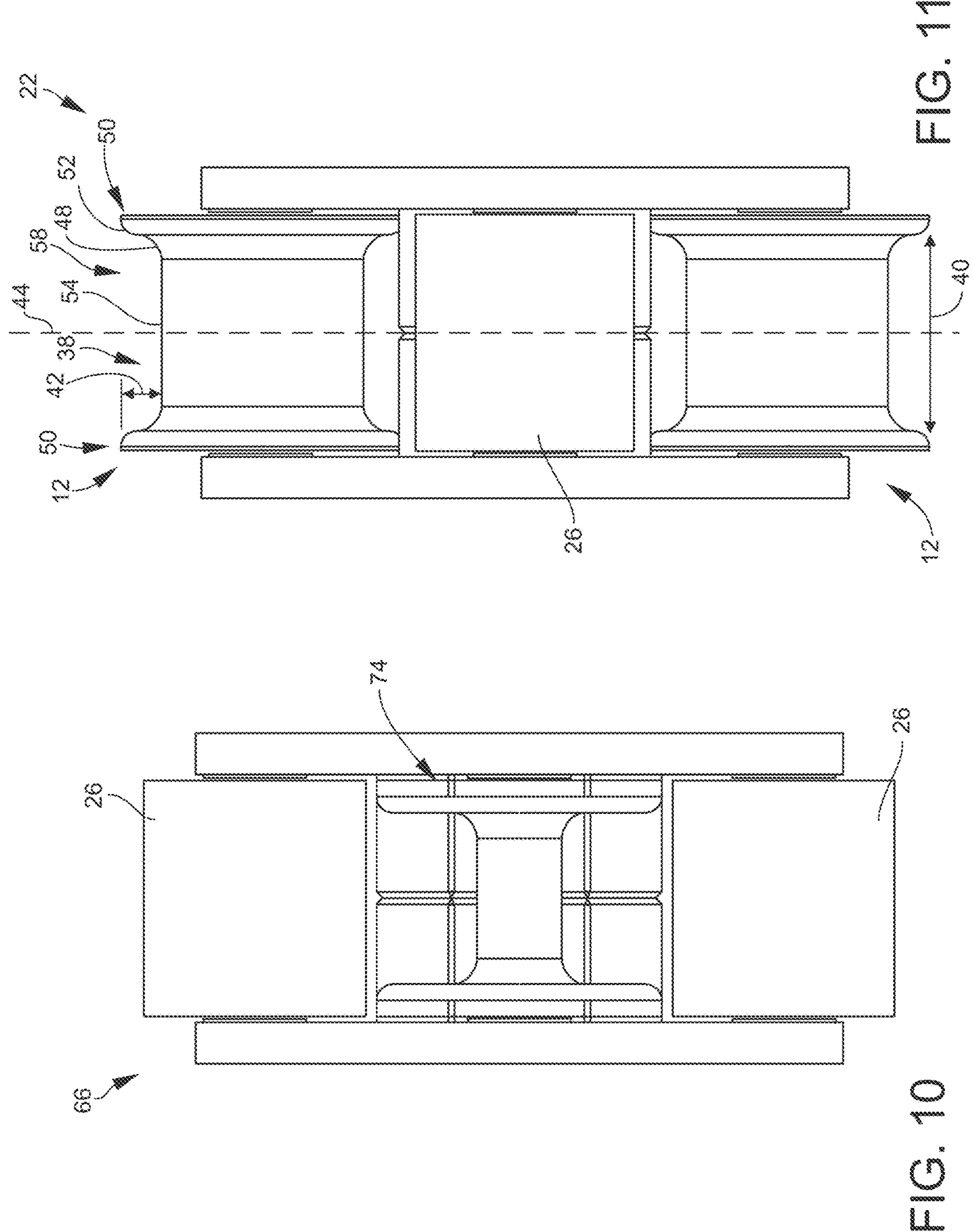
FIG. 10 is a top view of the roller assembly from FIG. 4 with compression rollers and guide rollers.
FIG. 11 is a top view of the roller assembly from FIG. 5 with compression rollers and hybrid rollers.
Figures 12, 13:
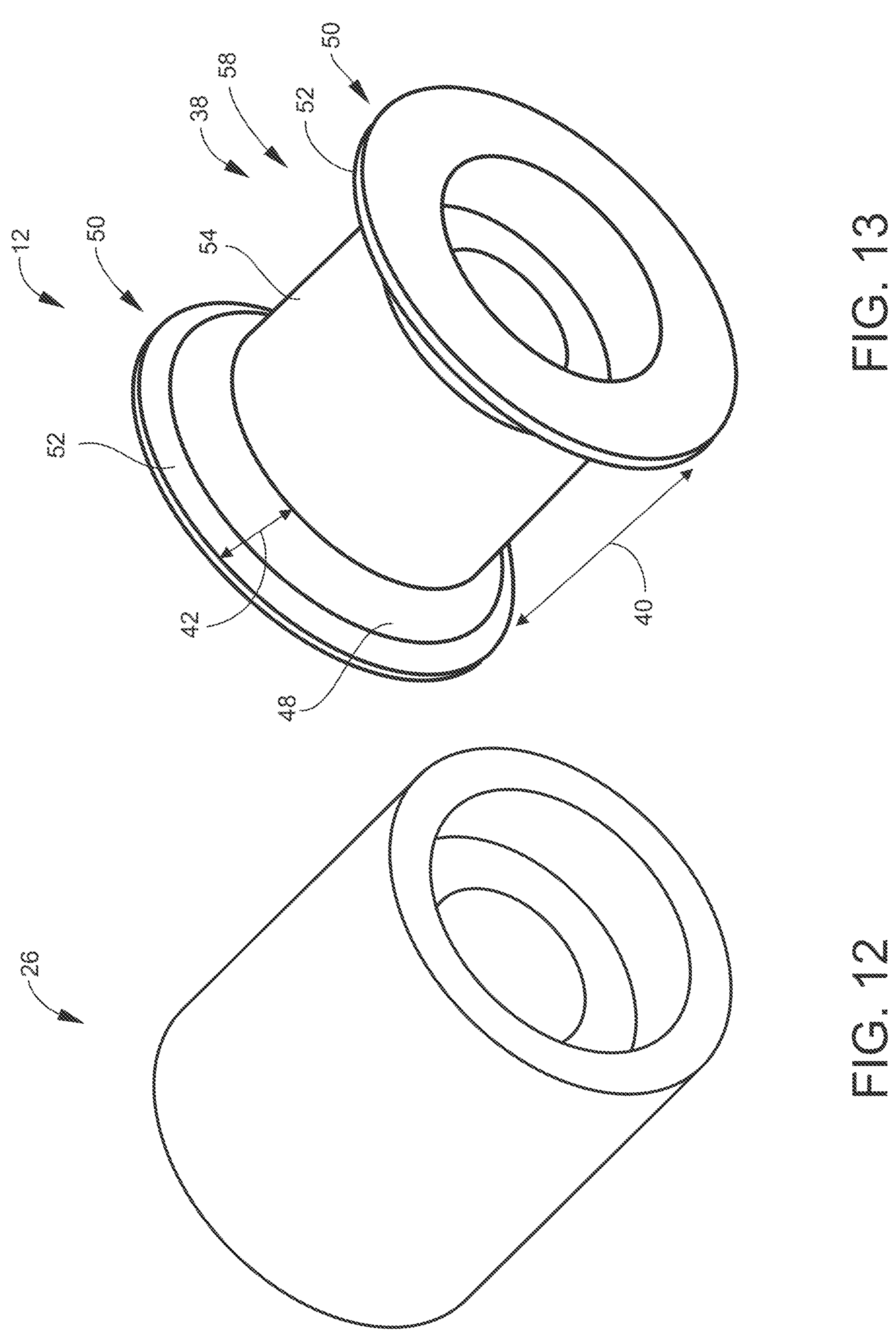
FIG. 12 is a perspective view of a compression roller for the roller assembly of the disclosed peristaltic pump head according to select embodiments of the instant disclosure.
FIG. 13 is a perspective view of a hybrid roller for the roller assembly of the disclosed peristaltic pump head according to select embodiments of the instant disclosure.
Figure 14:
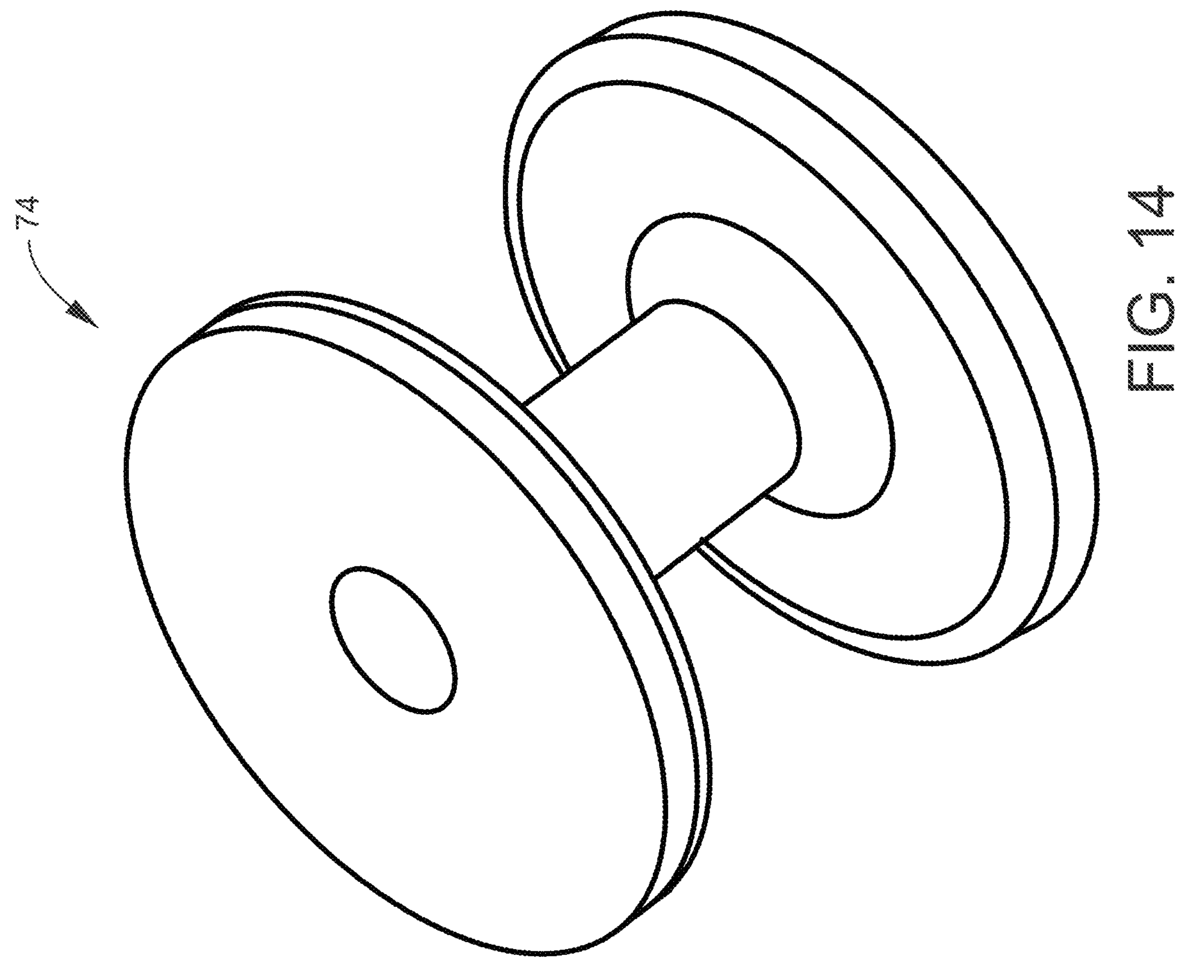
FIG. 14 is a perspective view of a guide roller for the roller assembly of the disclosed peristaltic pump head according to select embodiments of the instant disclosure.

In select embodiments of peristaltic pump head 10, as shown best in FIGS. 4, 6 and 9, the number of guide rollers 74 in second roller assembly 66 may be equal to the number of the compression rollers 26 in the second roller assembly 66. Whereby, one guide roller 74 may be peripherally spaced between every compression roller 26 in second roller assembly 66. As shown in the Figures, is select possibly preferred embodiments, two compression rollers 26 and two guide rollers 74 may be included with second roller assembly 66.

As shown best in FIG. 1, one feature of peristaltic pump head 10 may be that first roller assembly 22 and second roller assembly 66 can be controlled by single motor 77 with a single controller 78. Whereby, the speed of rotation of first roller assembly 22 and second roller assembly 66 may be the same. In select embodiments of peristaltic pump head 10, first housing 16 with first roller assembly 22 of compression rollers 26 and hybrid rollers 12 may be configured for feeding fluid 32 to system 82 (like a rotogravure printing press, or the like) via first flexible tube 18. On the other hand, second housing 60 with second roller assembly 66 of compression rollers 26 and guide rollers 74 may be configured for returning fluid 32 from system 82 via second flexible tube 62. Wherein volumetric fluid flow rate 84 may be created between fluid 32 moving in first flexible tube 18 (feeding system 82) via first roller assembly 22 and fluid 32 moving in second flexible tube 62 (returning from system 82) via second roller assembly 66. The volumetric fluid flow rate created between fluid 32 moving in first flexible tube 18 via first roller assembly 22 and fluid 32 moving in second flexible tube 62 via second roller assembly 66may be provided at any given speed 80 of motor 77. In select embodiments, volumetric fluid flow rate 84 created between fluid 32 moving in first flexible tube 18 (feeding system 82) via first roller assembly 22 and fluid 32 moving in second flexible tube 62 (returning from system 82) via second roller assembly 66 may be ten percent (10%) to fifteen percent (15%) greater in the fluid moving in second flexible tube 62 (returning) than the fluid moving in first flexible tube 18 (feeding).

Figure 23:
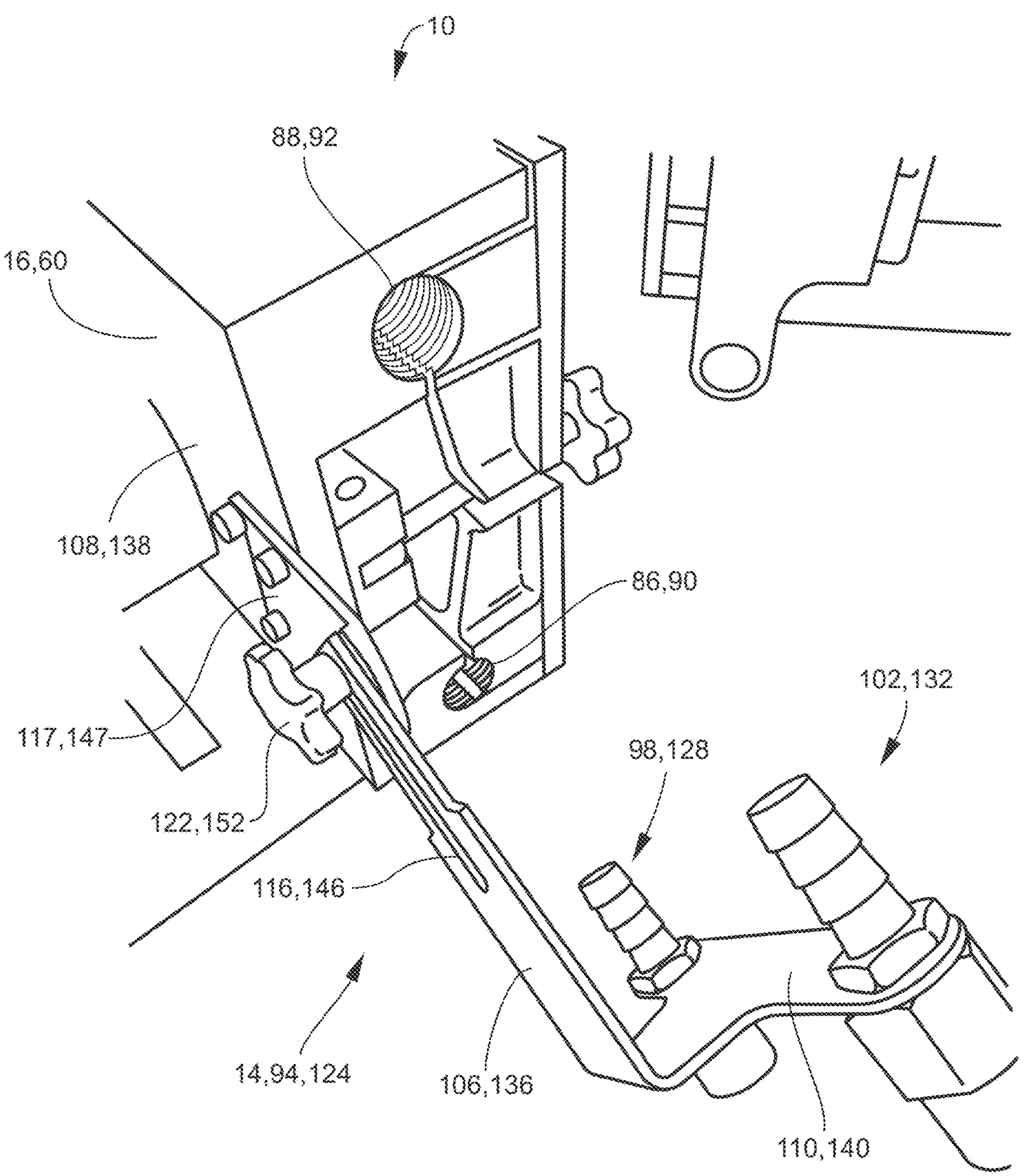
FIG. 23 is a side perspective view of the pump head with the tubing manifold attached thereto for the disclosed peristaltic pump head according to select embodiments of the instant disclosure with the tubing manifold rotated away from the pump head for changing the flexible tubing.

Another feature of peristaltic pump head 10 may be that first housing 16 may be adapted to load first flexible tube 18. Whereby, when first flexible tube 18 is inserted into first entrance 86 and first roller assembly 33 is rotated, hybrid rollers 12 and compression rollers 26 may guide first flexible tube 18 around first roller assembly 22 and out of first exit 88. Likewise, second housing 60 may be adapted to load second flexible tube 62. Whereby, when second flexible tube 62 is inserted into second entrance 90 and second roller assembly 66 is rotated, guide rollers 74 and compression rollers 26 guiding second flexible tube 62 around second roller assembly 66 and out of second exit 92. As best shown in FIG. 23, first entrance 86 and second entrance 90 may include a taper in the ribbed clamping section configured to grip the first flexible tube 18 and second flexible tube 62, respectively in a first orientation. Likewise, still best shown in FIG. 23, first exit 88 and second exit 92 may include a taper in the ribbed clamping section configured to grip the first flexible tube 18 and second flexible tube 62, respectively, in a second orientation. These tapered clamps in the entrances and exits may aid in auto-feeding of the flexible tube into the housing at the respective entrance around the roller assembly and out of the housing at the exit.

Referring now specifically to FIGS. 1-3 and 18-23, another feature of the disclosed peristaltic pump head 10 may be the inclusion of tubing manifold 14 or multiple tubing manifolds 14. As shown in the Figures, first tubing manifold 94 may be included with first housing 16 and second tubing manifold 124 may be included with second housing 60. First tubing manifold 94 may be configured for allowing fixed length 96 of first flexible tube 18 in first housing 16 by providing fixed connection point 98 for first end 100 of first flexible tube 18 about first entrance 86 of first housing 16 and fixed connection point 102 for second end 104 of first flexible tube 18 about first exit 88 of first housing 16. In select embodiments, first tubing manifold 94 may include first bracket 106 attached to first side 108 of first housing 16. First bracket 106 may extend from first side 108 of first housing 16 away from first entrance 86 and first exit 88. First mounting flange 110 may extend perpendicular to first bracket 106 in front of first entrance 86 and first exit 88. Fixed connection point 98 for first end 100 of first flexible tube 18 and fixed connection point 102 for second end 104 of first flexible tube 18 may be attached or affixed on first mounting flange 110. Wherein, first mounting flange 110 may be configured to position fixed connection point 98 for first end 100 of first flexible tube 18 in line with first entrance 86 of first housing 16 and fixed connection point 102 for second end 104 of first flexible tube 18 in line with first exit 88 of first housing 16.

One feature of peristaltic pump head 10 may be that first bracket 106 of first tubing manifold 94 may include first adjustable connection 112 to first side 108 of first housing 16. First adjustable connection 112 may be configured for allowing first bracket 106 to adjust first mounting flange 110 towards and away from first housing 16. Whereby, first connection length 114 can be adjusted between fixed connection point 98 for first end 100 of first flexible tube 18 and first entrance 86 of first housing 16, and fixed connection point 102 for second end 104 of first flexible tube 18 and first exit 88 of first housing 16. Whereby, first bracket 106 may be adjusted for properly tensioning first flexible tube 18 around first roller assembly 22.

Another feature of peristaltic pump head 10 may be that first adjustable connection 112 of first bracket 106 to first side 108 of first housing 16 may be configured to allow first bracket 106 to rotate about first side 108 of first housing 16. See FIGS. 20 and 23. Wherein, first bracket 106 rotating up or down about first side 108 of first housing 16 may be configured to aid in allowing the changing out of first flexible tube 18 from first housing 16.

First adjustable connection 112 may include any means, devices or mechanisms for creating an adjustable connection between first bracket 106 and first side 108 of first housing 16. In select embodiments, and clearly not limited thereto, as shown in the Figures, first adjustable connection 112 of first tubing manifold 94 to first side 108 of first housing 16 may include first longitudinal slot 116, first base plate 117 with first threaded hole 118, and first screw 120 with first knob handle 122. First longitudinal slot 116 may be in first bracket 106 of first tubing manifold 94. First base plate 117 may be affixed to first side 108 of first housing 16 with first threaded hole 118 therein. First screw 120 with first knob handle 122 may be configured to go through first longitudinal slot 116 and engage first threaded hole 118 in first base plate 117. Wherein, first screw 120 may be configured to be screwed into first threaded hole 118 via first knob handle 122 for securely affixing first bracket 106 about first side 108 of first housing 16. In reverse, first screw 120 may be configured to be loosened via first knob handle 122 for adjusting first mounting flange 110 towards and away from first housing 16, and/or for rotating first bracket 106 about first side 108 of first housing 16, like for aiding in accessing and changing out of first flexible tube 18 from first housing 16.

As shown with the Figures, in select embodiments of peristaltic pump head 10, first tubing manifold 94 may be included with first housing 16 and second tubing manifold 124 may be included with second housing 60. Second tubing manifold 124 may be configured for allowing fixed length 126 of second flexible tube 62 in second housing 60 by providing fixed connection point 128 for first end 130 of second flexible tube 62 about second entrance 90 of second housing 60 and fixed connection point 132 for second end 134 of second flexible tube 62 about second exit 92 of second housing 60. In select embodiments, second tubing manifold 124 may include second bracket 136 attached to second side 138 of second housing 60. Second bracket 136 may extend from second side 138 of second housing 60 away from second entrance 90 and second exit 92. Second mounting flange 140 may extend perpendicular to second bracket 136 in front of second entrance 90 and second exit 92. Fixed connection point 128 for the first end of the second flexible tube 62 and the fixed connection point 132 for the second end 134 of the second flexible tube 62 may be attached or affixed on second mounting flange 140. Wherein, second mounting flange 140 may be configured to position fixed connection point 128 for the first end 130 of the second flexible tube 62 in line with the second entrance 90 of second housing 60 and fixed connection point 132 for second end 134 of second flexible tube 62 in line with second exit 92 of second housing 60.

One feature of peristaltic pump head 10 may be that second bracket 136 of second tubing manifold 124 may include second adjustable connection 142 to second side 138 of second housing 60. Second adjustable connection 142 may be configured for allowing second bracket 136 to adjust second mounting flange 140 towards and away from second housing 60. Whereby, second connection length 144 can be adjusted between fixed connection point 128 for first end 130 of second flexible tube 62 and second entrance 90 of second housing 60, and fixed connection point 132 for second end 134 of second flexible tube 62 and second exit 92 of second housing 60. Whereby, second bracket 136 may be adjusted for properly tensioning second flexible tube 62 around second roller assembly 66 in second housing 60.

Another feature of peristaltic pump head 10 may be that second adjustable connection 142 of second bracket 136 to second side 138 of second housing 60 may be configured to allow second bracket 136 to rotate about second side 138 of second housing 60. Wherein, second bracket 136 rotating up or down about second side 138 of second housing 60 may be configured to aid in allowing the changing out of second flexible tube 62 from second housing 60.

Second adjustable connection 142 may include any means, devices or mechanisms for creating an adjustable connection between second bracket 136 and second side 138 of second housing 60. In select embodiments, and clearly not limited thereto, as shown in the Figures, second adjustable connection 142 of second tubing manifold 124 to second side 138 of second housing 60 may include second longitudinal slot 146, second base plate 147 with second threaded hole 148 therein, and second screw 150 with second knob handle 152. Second longitudinal slot 146 may be in second bracket 136 of second tubing manifold 124. Second base plate 147 may be affixed to second side 138 of second housing 60 with second threaded hole 148 therein. Second screw 150 with second knob handle 152 may be configured to go through second longitudinal slot 146 and engage second threaded hole 148 in second base plate 147. Wherein, second screw 150 may be configured to be screwed into second threaded hole 148 via second knob handle 152 for securely affixing second bracket 136 about second side 138 of second housing 60. In reverse, second screw 150 may be configured to be loosened via second knob handle 152 for adjusting second mounting flange 140 towards and away from second housing 60, and/or for rotating second bracket 136 about second side 138 of second housing 60, like for aiding in accessing and changing out of second flexible tube 62 from second housing 60.

In another aspect, the instant disclosure embraces peristaltic pump head 10 in any of the various embodiments and/or combinations of embodiments shown and/or described herein.

In another aspect, the instant disclosure embraces a peristaltic pump with peristaltic pump head 10 in any of the various embodiments and/or combinations of embodiments shown and/or described herein.

In sum, the disclosed peristaltic pump head 10 may be provided with various embodiments and/or combinations of embodiments with hybrid rollers 12 and/or tubing manifold (s) 14. The hybrid rollers 12 used herein provide a unique type of roller for roller assemblies in peristaltic pump heads. Typical compression rollers, like compression rollers 26 used herein, by design completely compresses the tubing, eliminating void between tubing walls, as it rotates and creates fluid suction and fluid pushing. Guide rollers, like guide rollers 74 used herein, are designed to keep tubing centered within the pump head, and do not compress the flexible tubing in any way. The disclosed hybrid rollers 12 may be unique in that they are a mixture of a compression roller, like compression rollers 26, and a guide roller, like guide rollers 74. Hybrid rollers 12 disclosed herein may be designed and configured to only partially compress the flexible tubing. Utilizing these hybrid rollers 12 in the two head design shown herein, volumetric fluid flow rate 84 may be provided with the difference between the two pump heads at any given speed or rpm of the motor. For example, in the printing industry, the goal may be to try and achieve a 10 to 15% greater flow rate on the head used to return from the system vs. the head used to feed the system. In addition, there is a benefit to use single motor 77 with single controller 78 to both feed and return from the system instead of having to use two separate pump/motor/controllers for each application. As such, the disclosed feeding system will use a spool (first roller assembly 22) with 2 compression rollers 26 and 2 hybrid rollers 12. And the disclosed returning from system will use a spool (second roller assembly 66) with 2 compression rollers 26 and 2 guide rollers 74.

Furthermore, the disclosed peristaltic pump 10 discloses the use of tubing manifold 14 or multiple tubing manifolds 14, like first tubing manifold 94 for first housing 16 and second tubing manifold 124 for second housing 60. The disclose tubing manifolds 14 may be designed to allow for use of a fixed length of peristaltic tubing in the pump head(s). The disclosed tubing manifold(s) 14 are also designed to help ensure a desired amount of tubing is placed and maintained within each pump head or housing. If insufficient tubing is used within a pump head, the tubing can be partially compressed so it does not fully open to design inside diameter. This would reduce the volume of flow per full rotation of the pump spool. It also will put extra stress on the tubing causing it to wear and fail quicker. Typically, one would use peristaltic tubing within the pump, then transition to a cheaper transfer hose to run between the pump and system the fluid is being delivered to. By nature of how it is used, the peristaltic tubing will wear out and need to be replaced more frequently. The hose between the pump and system does not need to be changed. The disclosed tubing manifold(s) 14 may be designed to provide a rigid/supported connection point to transition from peristaltic tubing to transfer hose. As such, the disclosed tubing manifold may increase the life of peristaltic tubing, like first flexible tube 18 and/or second flexible tube 62 used in the disclosed peristaltic pump head 10. Without tubing manifold (s) 14 manifold, the weight of pipe fittings and transfer hose put extra strain/stress on the peristaltic tube typically causing it to stretch thus failing quicker. Each tubing manifold 14 may include a base plate, a sliding and rotating bracket, and tubing connections on a mounting flange. The base plate may mount to the pump head. The attached tubing connections may be, but are not limited to, hose barbs, as shown herein. With the disclosed tubing manifold(s) 14, two peristaltic connection points are provided that are lined up with the entrance and exit of the respective pump head housing. When installing new peristaltic tubing, using the sliding mechanism of the adjustable connection of the tubing manifold 14, the fixed connection points may be slid away from the pump head to give enough space to change out and install new tubing. It can then be slid back towards the pump head and locked at the "zero" position during normal pump operation Furthermore, the disclosed peristaltic pump head 10 provides for a taper to the inside portion of the pump body ribbed clamping section. One of the benefits of the disclosed pump head 10 may be that the tubing can be auto-fed into and through the head/body. By cracking the door and turning the pump on, tubing can be manually fed into the entrance side of the pump head. With the roller assembly in rotation, the tubing will make its way through the head and eventually come out the exit side. The hinged door can then be closed and secured so the clamping mechanisms will hold the tubing in place. A typical peristaltic pump requires you to remove parts like the spool or roller assembly to load the tubing, which is obviously much more time consuming and labor intensive. The adding of the tapered section to the clamping section helps direct the tubing to the outlet, helping ensure it doesn't get caught up inside.

In the specification and/or figures, typical embodiments of the disclosure have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herein but is limited only by the following claims.

The invention claimed is:

1. A peristaltic pump head comprising:

a first housing being adapted to receive a first flexible tube having a first curved wall, said first housing being adapted to secure said first flexible tube within said first housing;

a first roller assembly being rotatable within said first housing about a first axis through said first housing, said first axis being coaxial to said first curved wall, said first roller assembly comprising:

at least two compression rollers being peripherally spaced where each of said compression rollers coming successively into contact with said first flexible tube during rotation of said first roller assembly with successive compression rollers being operative to compress two portions of said first flexible tube against said first curved wall to confine a first finite volume of a fluid in said first flexible tube;

at least one hybrid roller being peripherally spaced between said compression rollers where each of said hybrid rollers coming into contact with said first flexible tube during rotation of said first roller assembly with said hybrid rollers being operative to partially decompress said first flexible tube and guide said first flexible tube to stay centered with said compression rollers, said hybrid rollers being operative to initiate decompression of said first flexible tube to return to a partial compression dimension;

whereby the fluid in said first flexible tube is moved through said first flexible tube by rotation of said first roller assembly;

a second housing being adapted to receive a second flexible tube having a second curved wall, said second housing being adapted to secure said second flexible tube within said second housing;

a second roller assembly being rotatable within said second housing about a second axis through said second housing, said second axis being coaxial to said second curved wall, said second roller assembly comprising:

at least two of the compression rollers being peripherally spaced where each of said compression rollers coming successively into contact with said second flexible tube during rotation of said second roller assembly with successive compression rollers being operative to compress two portions of said second flexible tube against said second curved wall to confine a second finite volume of the fluid in said second flexible tube;

at least one guide roller being peripherally spaced between said compression rollers, where each of said guide rollers coming into contact with said second flexible tube during rotation of said second roller assembly with said guide rollers being operative to fully decompress said second flexible tube and guide said second flexible tube to stay centered with said compression rollers, said guide rollers being operative to initiate decompression of said second flexible tube to return to a fully uncompressed dimension; and whereby the fluid in said second flexible tube is moved through said second flexible tube by rotation of said second roller assembly.

2. The peristaltic pump head of claim 1, wherein:

said hybrid rollers having a channel with a width and a depth;

said width being centered on said hybrid rollers for guiding said first flexible tube to stay centered with said compression rollers on a first horizontal plane;

said depth being configured for allowing partial decompression of said first flexible tube to said partial compression dimension; and said width being at least the width of said first flexible tube at said partial compression dimension initiating decompression of said flexible tube to return to said partial compression dimension.

3. The peristaltic pump head of claim 2, wherein said partial compression dimension being when said first flexible tube being compressed approximately fifty percent (50%).

4. The peristaltic pump head of claim 2, wherein said hybrid rollers including a rounded transition on both sides of the channel between walls of the channel and a bottom of the channel, the rounded transition on both sides of the channel are sized and configured for the first flexible tube at said partial compression dimension.

5. The peristaltic pump head of claim 4, wherein the walls of said channel, the rounded transition of said channel, the bottom of said channel, or a combination thereof, including an anti-friction surface, said anti-friction surface on the walls of said channel, the rounded transition of said channel, the bottom of said channel, or a combination thereof is configured for aiding said hybrid rollers to move along said first flexible tube.

6. The peristaltic pump head of claim 1, wherein a number of said at least one hybrid roller in said first roller assembly is equal to a number of the compression rollers in said first roller assembly, where one hybrid roller being peripherally spaced between every compression roller in said first roller assembly.

7. The peristaltic pump head of claim 1, wherein the first roller assembly and the second roller assembly are controlled by a single motor with a single controller, whereby a speed of rotation of the first roller assembly and a speed of rotation of the second roller assembly are the same.

8. The peristaltic pump head of claim 7, wherein:

the first housing with the first roller assembly of compression rollers and hybrid rollers is configured for feeding the fluid to a system via the first flexible tube;

the second housing with the second roller assembly of compression rollers and guide rollers, is configured for returning the fluid from the system via the second flexible tube;

wherein a volumetric fluid flow rate is created between the fluid moving in the first flexible tube via the first roller assembly and the fluid moving in the second flexible tube via the second roller assembly; and wherein the volumetric fluid flow rate created between the fluid moving in the first flexible tube via the first roller assembly and the fluid moving in the second flexible tube via the second roller assembly is provided at any given speed of the motor.

9. The peristaltic pump head of claim 8, wherein the volumetric fluid flow rate created between the fluid moving in the first flexible tube via the first roller assembly and the fluid moving in the second flexible tube via the second roller assembly is at least ten percent (10%) greater in the fluid moving in the second flexible tube than the fluid moving in the first flexible tube.

10. The peristaltic pump head of claim 1, wherein said first housing being adapted to load said first flexible tube, whereby, when said first flexible tube is inserted into a first entrance and said first roller assembly is rotated, said hybrid rollers and said compression rollers guiding said first flexible tube around said first roller assembly and out of a first exit;

said second housing being adapted to load said second flexible tube, whereby, when said second flexible tube is inserted into a second entrance and said second roller assembly is rotated, said guide rollers and said compression rollers guiding said second flexible tube around said second roller assembly and out of a second exit; or a combination thereof.

11. The peristaltic pump head of claim 1 further including a first tubing manifold with the first housing, the first tubing manifold is configured for allowing a fixed length of said first flexible tube in the first housing by providing a fixed connection point for a first end of the first flexible tube about a first entrance of the first housing and a fixed connection point for a second end of the first flexible tube about a first exit of the first housing.

12. The peristaltic pump head of claim 11, wherein the first tubing manifold including:

a first bracket attached to a first side of the first housing, the first bracket extending from the first side of the first housing away from the first entrance and the first exit;

a first mounting flange extending perpendicular to the first bracket in front of the first entrance and the first exit;

the fixed connection point for the first end of the first flexible tube and the fixed connection point for the second end of the first flexible tube are attached on the first mounting flange, wherein the first mounting flange is configured to position the fixed connection point for the first end of the first flexible tube in line with the first entrance of the first housing and the fixed connection point for the second end of the first flexible tube in line with the first exit of the first housing;

wherein the first bracket of the first tubing manifold including a first adjustable connection to the first side of the first housing, the first adjustable connection is configured for allowing the first bracket to adjust the first mounting flange towards and away from the first housing, whereby a first connection length can be adjusted between the fixed connection point for the first end of the first flexible tube and the first entrance of the first housing and the fixed connection point for the second end of the first flexible tube and the first exit of the first housing, whereby the first bracket is configured to be adjusted for properly tensioning the first flexible tube around the first roller assembly; and wherein the first adjustable connection of the first bracket to the first side of the first housing is configured to allow the first bracket to rotate about the first side of the first housing, wherein the first bracket rotating up or down about the first side of the first housing is configured to aid in allowing the changing out of the first flexible tube from the first housing.

13. The peristaltic pump head of claim 12, wherein the first adjustable connection of the first tubing manifold to the first side of the first housing including:

a first longitudinal slot in the first bracket of the first tubing manifold;

a first base plate affixed to the first side of the first housing with a first threaded hole therein; and a first screw with a first knob handle configured to go through the first longitudinal slot and engage the first threaded hole in the first base plate, wherein, the first screw is configured to be screwed into the first threaded hole via the first knob handle for securely affixing the first bracket about the first side of the first housing, and the first screw is configured to be loosened via the first knob handle for adjusting the first mounting flange towards and away from the first housing, or for rotating the first bracket about the first side of the first housing for changing out of the first flexible tube from the first housing.

14. The peristaltic pump head of claim 1 further including:

a first tubing manifold with the first housing, the first tubing manifold is configured for allowing a fixed length of said first flexible tube in the first housing by providing a fixed connection point for a first end of the first flexible tube about a first entrance of the first housing and a fixed connection point for a second end of the first flexible tube about a first exit of the first housing; and a second tubing manifold with the second housing, the second tubing manifold is configured for allowing a fixed length of said second flexible tube in the second housing by providing a fixed connection point for a first end of the second flexible tube about a second entrance of the second housing and a fixed connection point for a second end of the second flexible tube about a second exit of the second housing.

15. The peristaltic pump head of claim 14, wherein:

the first tubing manifold including:

a first bracket attached to a first side of the first housing, the first bracket extending from the first side of the first housing away from the first entrance and the first exit;

a first mounting flange extending perpendicular to the first bracket in front of the first entrance and the first exit;

the fixed connection point for the first end of the first flexible tube and the fixed connection point for the second end of the first flexible tube are attached on the first mounting flange, wherein the first mounting flange is configured to position the fixed connection point for the first end of the first flexible tube in line with the first entrance of the first housing and the fixed connection point for the second end of the first flexible tube in line with the first exit of the first housing;

the first bracket of the first tubing manifold including a first adjustable connection to the first side of the first housing, the first adjustable connection is configured for allowing the first bracket to adjust the first mounting flange towards and away from the first housing, whereby a first connection length can be adjusted between the fixed connection point for the first end of the first flexible tube and the first entrance of the first housing and the fixed connection point for the second end of the first flexible tube and the first exit of the first housing, whereby the first bracket is configured to be adjusted for properly tensioning the first flexible tube around the first roller assembly;

the first adjustable connection of the first bracket to the first side of the first housing is configured to allow the first bracket to rotate about the first side of the first housing, wherein the first bracket rotating up or down about the first side of the first housing is configured to aid in allowing the changing out of the first flexible tube from the first housing;

the first adjustable connection of the first tubing manifold to the first side of the first housing including:

a first longitudinal slot in the first bracket of the first tubing manifold;

a first base plate affixed to the first side of the first housing with a first threaded hole therein;

a first screw with a first knob handle configured to go through the first longitudinal slot and engage the first threaded hole in the first base plate, wherein, the first screw is configured to be screwed into the first threaded hole via the first knob handle for securely affixing the first bracket about the first side of the first housing, and the first screw is configured to be loosened via the first knob handle for adjusting the first mounting flange towards and away from the first housing, or for rotating the first bracket about the first side of the first housing for changing out of the first flexible tube from the first housing;

the second tubing manifold including:

a second bracket attached to a second side of the second housing, the second bracket extending from the second side of the second housing away from the second entrance and the second exit;

a second mounting flange extending perpendicular to the second bracket in front of the second entrance and the second exit;

the fixed connection point for the first end of the second flexible tube and the fixed connection point for the second end of the second flexible tube are attached on the second mounting flange, wherein the second mounting flange is configured to position the fixed connection point for the first end of the second flexible tube in line with the second entrance of the second housing and the fixed connection point for the second end of the second flexible tube in line with the second exit of the second housing;

the second bracket of the second tubing manifold including a second adjustable connection to the second side of the second housing, the second adjustable connection is configured for allowing the second bracket to adjust the second mounting flange towards and away from the second housing, whereby a second connection length can be adjusted between the fixed connection point for the first end of the second flexible tube and the second entrance of the second housing and the fixed connection point for the second end of the second flexible tube and the second exit of the second housing, whereby the second bracket is configured to be adjusted for properly tensioning the second flexible tube around the second roller assembly;

the second adjustable connection of the second bracket to the second side of the second housing is configured to allow the second bracket to rotate about the second side of the second housing, wherein the second bracket rotating up or down about the second side of the second housing is configured to aid in allowing the changing out of the second flexible tube from the second housing;

the second adjustable connection of the second tubing manifold to the second side of the second housing including:

a second longitudinal slot in the second bracket of the second tubing manifold;

a second based plate affixed to the second side of the second housing with a second threaded hole therein; and a second screw with a second knob handle configured to go through the second longitudinal slot and engage the second threaded hole in a second base plate, wherein, the second screw is configured to be screwed into the second threaded hole via the second knob handle for securely affixing the second bracket about the second side of the second housing, and the second screw is configured to be loosened via the second knob handle for adjusting the second mounting flange towards and away from the second housing, or for rotating the second bracket about the second side of the second housing for changing out of the second flexible tube from the second housing.

16. A peristaltic pump head comprising:

a first housing being adapted to receive a first flexible tube having a first curved wall, said first housing being adapted to secure said first flexible tube within said first housing;

a first roller assembly being rotatable within said first housing about a first axis through said first housing, said first axis being coaxial to said first curved wall, said first roller assembly comprising:

at least two compression rollers being peripherally spaced where each of said compression rollers coming successively into contact with said first flexible tube during rotation of said first roller assembly with successive compression rollers being operative to compress two portions of said first flexible tube against said first curved wall to confine a first finite volume of a fluid in said first flexible tube;

whereby the fluid in the first flexible tube is moved through said first flexible tube by rotation of said first roller assembly; and a first tubing manifold with the first housing, the first tubing manifold is configured for allowing a fixed length of said first flexible tube in the first housing by providing a fixed connection point for a first end of the first flexible tube about a first entrance of the first housing and a fixed connection point for a second end of the first flexible tube about a first exit of the first housing;

wherein the first tubing manifold including:

a first bracket attached to a first side of the first housing, the first bracket extending from the first side of the first housing away from the first entrance and the first exit;

a first mounting flange extending perpendicular to the first bracket in front of the first entrance and the first exit;

the fixed connection point for the first end of the first flexible tube and the fixed connection point for the second end of the first flexible tube are attached on the first mounting flange, wherein the first mounting flange is configured to position the fixed connection point for the first end of the first flexible tube in line with the first entrance of the first housing and the fixed connection point for the second end of the first flexible tube in line with the first exit of the first housing;

wherein:

the first bracket of the first tubing manifold including a first adjustable connection to the first side of the first housing, the first adjustable connection is configured for allowing the first bracket to adjust the first mounting flange towards and away from the first housing, whereby a first connection length can be adjusted between the fixed connection point for the first end of the first flexible tube and the first entrance of the first housing and the fixed connection point for the second end of the first flexible tube and the first exit of the first housing, whereby the first bracket is configured to be adjusted for properly tensioning the first flexible tube around the first roller assembly;

the first adjustable connection of the first bracket to the first side of the first housing is configured to allow the first bracket to rotate about the first side of the first housing, wherein the first bracket rotating up or down about the first side of the first housing is configured to aid in allowing the changing out of the first flexible tube from the first housing;

wherein the first adjustable connection of the first tubing manifold to the first side of the first housing including:

a first longitudinal slot in the first bracket of the first tubing manifold;

a first base plate affixed to the first side of the first housing with a first threaded hole therein; and a first screw with a first knob handle configured to go through the first longitudinal slot and engage the first threaded hole in the first base plate, wherein, the first screw is configured to be screwed into the first threaded hole via the first knob handle for securely affixing the first bracket about the first side of the first housing, and the first screw is configured to be loosened via the first knob handle for adjusting the first mounting flange towards and away from the first housing, or for rotating the first bracket about the first side of the first housing for changing out of the first flexible tube from the first housing.

17. A peristaltic pump head comprising:

a first housing being adapted to receive a first flexible tube having a first curved wall, said first housing being adapted to secure said first flexible tube within said first housing;

a first roller assembly being rotatable within said first housing about a first axis through said first housing, said first axis being coaxial to said first curved wall, said first roller assembly comprising:

at least two compression rollers being peripherally spaced where each of said compression rollers coming successively into contact with said first flexible tube during rotation of said first roller assembly with successive compression rollers being operative to compress two portions of said first flexible tube against said first curved wall to confine a first finite volume of a fluid in said first flexible tube;

at least one hybrid roller being peripherally spaced between said compression rollers where each of said hybrid rollers coming into contact with said first flexible tube during rotation of said first roller assembly with said hybrid rollers being operative to partially decompress said first flexible tube and guide said first flexible tube to stay centered with said compression rollers, said hybrid rollers being operative to initiate decompression of said first flexible tube to return to a partial compression dimension;

whereby the fluid in the first flexible tube is moved through said first flexible tube by rotation of said first roller assembly; and a first tubing manifold with the first housing, the first tubing manifold is configured for allowing a fixed length of said first flexible tube in the first housing by providing a fixed connection point for a first end of the first flexible tube about a first entrance of the first housing and a fixed connection point for a second end of the first flexible tube about a first exit of the first housing, wherein the first tubing manifold including:

a first bracket attached to a first side of the first housing, the first bracket extending from the first side of the first housing away from the first entrance and the first exit;

a first mounting flange extending perpendicular to the first bracket in front of the first entrance and the first exit;

the fixed connection point for the first end of the first flexible tube and the fixed connection point for the second end of the first flexible tube are attached on the first mounting flange, wherein the first mounting flange is configured to position the fixed connection point for the first end of the first flexible tube in line with the first entrance of the first housing and the fixed connection point for the second end of the first flexible tube in line with the first exit of the first housing;

wherein the first bracket of the first tubing manifold including a first adjustable connection to the first side of the first housing, the first adjustable connection is configured for allowing the first bracket to adjust the first mounting flange towards and away from the first housing, whereby a first connection length can be adjusted between the fixed connection point for the first end of the first flexible tube and the first entrance of the first housing and the fixed connection point for the second end of the first flexible tube and the first exit of the first housing, whereby the first bracket is configured to be adjusted for properly tensioning the first flexible tube around the first roller assembly; and wherein the first adjustable connection of the first bracket to the first side of the first housing is configured to allow the first bracket to rotate about the first side of the first housing, wherein the first bracket rotating up or down about the first side of the first housing is configured to aid in allowing the changing out of the first flexible tube from the first housing.

* * * * *